(12) United States Patent
Sudo et al.

(10) Patent No.: US 8,585,752 B2
(45) Date of Patent: Nov. 19, 2013

(54) STENT AND STENT DELIVERY SYSTEM

(75) Inventors: Tomohiro Sudo, Fujinomiya (JP);
Kinya Harada, Fujinomiya (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 90 days.

(21) Appl. No.: 13/353,705

(22) Filed: Jan. 19, 2012

(65) Prior Publication Data

US 2012/0209366 A1 Aug. 16, 2012

(30) Foreign Application Priority Data

Feb. 15, 2011 (JP) .................................. 2011-30243

(51) Int. Cl.
*A61F 2/06* (2013.01)
(52) U.S. Cl.
USPC .......... 623/1.16; 623/1.15; 623/1.18; 623/1.2
(58) Field of Classification Search
USPC ................................ 623/1.15, 1.16, 1.18, 1.2
See application file for complete search history.

(56) References Cited

U.S. PATENT DOCUMENTS

| | | | | |
|---|---|---|---|---|
| 6,066,169 | A * | 5/2000 | McGuinness | 623/1.16 |
| 7,131,993 | B2 * | 11/2006 | Gregorich | 623/1.16 |
| 7,618,445 | B2 | 11/2009 | Moriuchi et al. | |
| 7,651,524 | B2 | 1/2010 | Moriuchi et al. | |
| 2007/0055353 | A1 | 3/2007 | Fliedner | |

FOREIGN PATENT DOCUMENTS

| | | |
|---|---|---|
| EP | 2 098 195 | 9/2009 |
| EP | 2 143 404 A1 | 1/2010 |
| JP | 2008 086464 A | 4/2008 |
| WO | 96/26689 | 9/1996 |
| WO | 97/32546 | 9/1997 |
| WO | 98/30173 | 7/1998 |
| WO | 99/65421 | 12/1999 |

OTHER PUBLICATIONS

Extended European Search Report issued on Jun. 18, 2012, by the European Patent Office in corresponding European Patent Application No. 12155459.6-1257. (11 pages).
European Communication issued Aug. 8, 2013 by the European Patent Office in corresponding European Patent Application No. 12155459.6 - 1257 (4 pgs).

* cited by examiner

*Primary Examiner* — Gary Jackson
*Assistant Examiner* — Michael Mendoza
(74) *Attorney, Agent, or Firm* — Buchanan Ingersoll & Rooney PC

(57) ABSTRACT

A stent includes a plurality of annular bodies arrayed in an axial direction, each having a plurality of one-end-side bent sections and other-end-side bent sections, and adjacent ones of the annular bodies being linked by link sections. The stent includes at least three kinds of link sections selected from four kinds of link sections including: a vertex-vertex bent link section; a central part-central part bent link section; a central part-vertex bent link section; and a vertex-central part bent link section, the at least three kinds of the link sections including at least the vertex-vertex bent link section and the central part-central part bent link section, and the adjacent annular bodies being linked by at least two different kinds of the link sections.

20 Claims, 26 Drawing Sheets

STENT AND STENT DELIVERY SYSTEM

RELATED APPLICATION DATA

This application claims the benefit of foreign priority to Japan 2011-30243 filed Feb. 15, 2011, and is hereby incorporated by reference in its entirety.

FIELD OF THE INVENTION

The present invention generally relates to a stent and a stent delivery system used to improve or treat a stenosed part or an occluded part in a living body lumen such as blood vessel, bile duct, trachea, esophagus, urethra and other organs.

BACKGROUND DISCUSSION

A stent is a tubular medical device which is used for therapy or treatment of various diseases arising from stenosis or occlusion of a living body lumen such as a blood vessel and, specifically, is set indwelling (i.e., is indwelled) in the stenosed part or occluded part so as to dilate the part and secure the lumen thereof. Since a stent is inserted into the living body from the outside, it is reduced in diameter at the time of insertion and, thereafter, it is expanded or restored to an enlarged diameter state in the target stenosed or occluded part, so as to secure the lumen while remaining in the enlarged diameter state. Stents are classified into self-expandable stents and balloon-expandable stents, depending on their function and manner of expansion. A balloon-expandable stent is a stent which itself does not have an expanding function; the stent mounted on a balloon is inserted into the target part, and thereafter the balloon is inflated to expand (plastically deform) the stent by the balloon's expansive force, thereby fixing the stent in close contact with the inner surface of the target lumen.

This type of stent needs the above-mentioned stent-expanding operation. On the other hand, a self-expandable stent is formed from a material having shape memory properties, and is produced in the size of an expanded final shape. In order to introduce a self-expandable stent into a living body, the stent in a small folded state is inserted into a member (mostly, a plastic-made tube) for restricting its shape, is then introduced into the living body together with the member, or tube, and is released from the tube at the target part, whereon the stent self-expands by its shape memory properties.

At present, the mainstream of self-expandable stents are stents formed in a substantially cylindrical hollow shape by interlinking at joints a plurality of annular bodies which are each formed in a substantially zigzag pattern by interconnecting a plurality of strut sections with a plurality of loop sections.

The self-expandable stent disclosed in WO 96/26689 (hereinafter referred to as Patent Document 1) has a structure in which wavy annular bodies are interconnected by connectors which are formed obliquely.

In addition, there are stents of the type in which vertexes of a meandering element or zigzag element enter into the adjacent meandering element or zigzag element. An example of this type of self-expandable stent includes the one disclosed in WO 97/32546 (hereinafter referred to as Patent Document 2). In the self-expandable stent disclosed in WO 99/65421 (hereinafter referred to as Patent Document 3), vertexes of the adjacent meandering elements as above-mentioned are interconnected by connectors parallel to the stent axis.

In addition, there are stents of the type in which meandering elements or zigzag elements are not in a plane loop form but in a spiral form. Examples of this type of stents include one composed of one or a plurality of spiral elements extending from the distal end to the proximal end thereof. For example, according to WO 98/30173 (hereinafter referred to as Patent Document 4), zigzag elements are interconnected by connectors parallel to the stent axis, for maintaining the shape of the stent. Further, as self-expandable stents in which adjacent annular bodies are partly integrated with each other by a shared linear section, the present inventors have proposed those disclosed in EP 2098195 A1 (hereinafter referred to as Patent Document 5), U.S. Pat. No. 7,651,524 B2 (hereinafter referred to as Patent Document 6) and U.S. Pat. No. 7,618,445 B2 (hereinafter referred to as Patent Document 7).

Stents are desired to have good compressibility permitting compression to an outside diameter as small as possible, a sufficient expansion-retaining force when expanded, and good trackability with respect to deformations of a living body lumen such as a blood vessel.

The stents of the types disclosed in the above-mentioned Patent Documents 1 to 4 have been insufficient in trackability with respect to deformations of a blood vessel, though sufficient in the expansion-retaining force. In addition, although the stents of the types disclosed in Patent Documents 5 to 7 have good effects, there is a demand for a stent which has better compressibility and better expansion-retaining force and trackability with respect to deformations of a blood vessel.

SUMMARY

The stent disclosed here exhibits good compressibility and sufficient expansion-retaining force, and has good trackability with respect to deformations of a living body lumen such as a blood vessel.

The stent is configured to be brought into contact with tissue in a living body through deformation at the time of indwelling the stent in the living body. The stent includes a plurality of annular bodies arrayed in an axial direction, with each of the annular bodies being annularly-shaped from a linear constituent element, and each having a plurality of one-end-side bent sections which are bent sections at one axial end and a plurality of other-end-side bent sections which are bent sections at an opposite axial end. Axially adjacent ones of the annular bodies are linked by link sections, and the stent includes, as the link sections, at least three kinds of link sections selected from four kinds of link sections. The four kinds of link sections include: a vertex-vertex bent link section which links a vertex of one of the other-end-side bent sections of the one-end-side annular body of the axially adjacent annular bodies with a vertex of one of the one-end-side bent sections of the other-end-side annular body of the axially adjacent annular bodies and which has at least one one-end-side bent part and at least one other-end-side bent part; a central part-central part bent link section which links a central part of a linear portion interconnecting the one-end-side bent section and the other-end-side bent section of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part; a central part-vertex bent link section which links the central part of the linear portion interconnecting the one-end-side bent section and the other-end-side bent section of the one-end-side annular body of the one annular bodies with the vertex of the one-end-side bent section of the other-end-side annular body of the axially adjacent annular body and which has at least one one-end-side bent part and at least one other-end-side bent part; and a vertex-central part bent link section which links the vertex of one of the other-end-side bent sections of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part, the at least three kinds of the link sections including at least the vertex-vertex bent link section and the central part-central part bent link section, and the axially adjacent annular bodies being linked by at least two different kinds of the four link sections.

All the axially adjacent annular bodies may be linked by three kinds of the link sections including the vertex-vertex bent link section, the central part-central part bent link section, and either the central part-vertex bent link section or the vertex-central part bent link section.

According to another variation, all the axially adjacent annular bodies may be linked by the four kinds of the link sections including the vertex-vertex bent link section, the central part-central part bent link section, the central part-vertex bent link section, and the vertex-central part bent link section.

The vertex-vertex bent link sections may be arranged in a spiral pattern with respect to the axial direction of the stent.

The central part-central part bent link sections may be arranged in a spiral pattern with respect to the axial direction of the stent.

The stent preferably has a first linkage form in which the axially adjacent annular bodies are linked by at least the vertex-vertex bent link section and the central part-central part bent link section and a second linkage form in which the axially adjacent annular bodies are linked by at least the central part-vertex bent link section and the vertex-central part bent link section, with the first linkage form and the second linkage form alternately repeating in the axial direction.

The vertex-vertex bent link section may have two one-end-side bent parts and two other-end-side bent parts.

The central part-central part bent link section may have only one one-end-side bent part and only one other-end-side bent part.

The central part-vertex bent link section and the vertex-central part bent link section may each have only one one-end-side bent part and only one other-end-side bent part.

The one-end-side-bent part of the link section axially overlaps with the other-end-side bend sections of the one-end-side annular body of the axially adjacent annular bodies, and the other-end-side-bent part of the link section axially overlaps with the one-end-side bend sections of the other-end-side annular body of the axially adjacent annular bodies.

The stent preferably has the link sections so arranged that the same kind of link sections are not continuously arrayed on a straight line in the axial direction of the stent.

The stent is preferably formed in a substantially cylindrical shape, is compressed toward its center axis when inserted into a living body, and is restored to its pre-compression shape through outward expansion when set indwelling in the living body.

Another aspect of the disclosure here involves a stent delivery system including a stent-containing tubular member, the stent as described in the preceding paragraphs contained in a distal portion of the stent-containing tubular member, and a releasing mechanism for releasing the stent via a distal end of the stent-containing tubular member.

The stent disclosed here thus includes a plurality of annular bodies arranged in an axial direction, with each of the annular bodies being formed in an annular shape from a linear constituent element and having a plurality of one-end-side bent sections and a plurality of other-end-side bent sections, with adjacent ones of the annular bodies being linked by link sections. The stent includes, as the link sections, at least three kinds of link sections selected from four kinds of link sections including: a vertex-vertex bent link section which links a vertex of an other-end-side bent section of the one-end-side annular body of adjacent annular bodies with a vertex of an one-end-side bent section of the other-end-side annular body of the adjacent annular bodies and which has at least one one-end-side bent part and at least one other-end-side bent part; a central part-central part bent link section which links a central part of a linear portion interconnecting an one-end-side bent section and an other-end-side bent section of the one-end-side annular body of adjacent annular bodies with a central part of a linear portion interconnecting an one-end-side bent section and an other-end-side bent section of the other-end-side annular body of the adjacent annular bodies and which has at least one one-end-side bent part and at least one other-end-side bent part; a central part-vertex bent link section which links a central part of a linear portion interconnecting an one-end-side bent section and an other-end-side bent section of the one-end-side annular body of adjacent annular bodies with a vertex of an one-end-side bent section of the other-end-side annular body of the adjacent annular bodies and which has at least one one-end-side bent part and at least one other-end-side bent part; and a vertex-central part bent link section which links a vertex of an other-end-side bent section of the one-end-side annular body of adjacent annular bodies with a central part of a linear portion interconnecting an one-end-side bent section and an other-end-side bent section of the other-end-side annular body of the adjacent annular bodies and which has at least one one-end-side bent part and at least one other-end-side bent part, the at least three kinds of the link sections including at least the vertex-vertex bent link section and the central part-central part bent link section, and the adjacent annular bodies being linked by at least two different kinds of the link sections.

According to another aspect, a stent to be brought into contact with tissue in a living body through deformation at the time of indwelling the stent in the living body comprises at least four axially arranged and axially adjacent annular bodies, with each of the at least four axially adjacent annular bodies being a wavy-shaped continuous linear member possessing: one-end-side bent sections, which are each a section of the linear member bent at a vertex on one axial end of the wavy-shaped linear member: and other-end-side bent sections which are each a section of the linear member bent at a vertex on an opposite axial end of the wavy-shaped linear member. The at least four axially adjacent annular bodies are connected to one another by link sections, and the stent includes as the link sections at least three different kinds of link sections selected from four different kinds of link sections. The four different kinds of link sections include: a vertex-vertex bent link section which connects the vertex of one of the other-end-side bent sections of the one-end-side annular body of the axially adjacent annular bodies with the vertex of one of the one-end-side bent sections of the other-end-side annular body of the axially adjacent annular bodies and which has at least one one-end-side bent part and at least one other-end-side bent part; a central part-central part bent link section which connects a central part of a linear portion interconnecting the one-end-side bent section and the other-end-side bent section of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part; a central part-vertex bent link section which connects the central part of the linear portion interconnecting the one-end-side bent section and the other-end-side bent section of the one-end-side annular body of the axially adjacent annular bodies with the vertex of one of the one-end-side bent sections of the other-end-side annular body of the axially adjacent annular bodies and which has at least one one-end-side bent part and at least one other-end-side bent part; and a vertex-central part bent link section which connects the vertex of one of the other-end-side bent sections of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part. The at least three kinds of the link sections include at least the vertex-vertex bent link section and the central part-central part bent link section, and the axially adjacent annular bodies being linked by at least two different kinds of the four link sections.

Particularly, by having the vertex-vertex bent link sections, the stent has flexibility and an easily compressible property. In addition, by providing the stent with the central part-central part bent link sections, a sufficient expansion-retaining force is imparted to the stent. By providing the stent with either the central part-vertex bent link sections or the vertex-central part bent link sections, properties which are intermediate between those of the vertex-vertex bent link sections and those of the central part-central part bent link sections are imparted to the stent. This ensures that the stent as a whole has good compressibility, a sufficient expansion-retaining force, and sufficient trackability with respect to deformations of a living body lumen such as a blood vessel.

DETAILED DESCRIPTION

Figure 1:
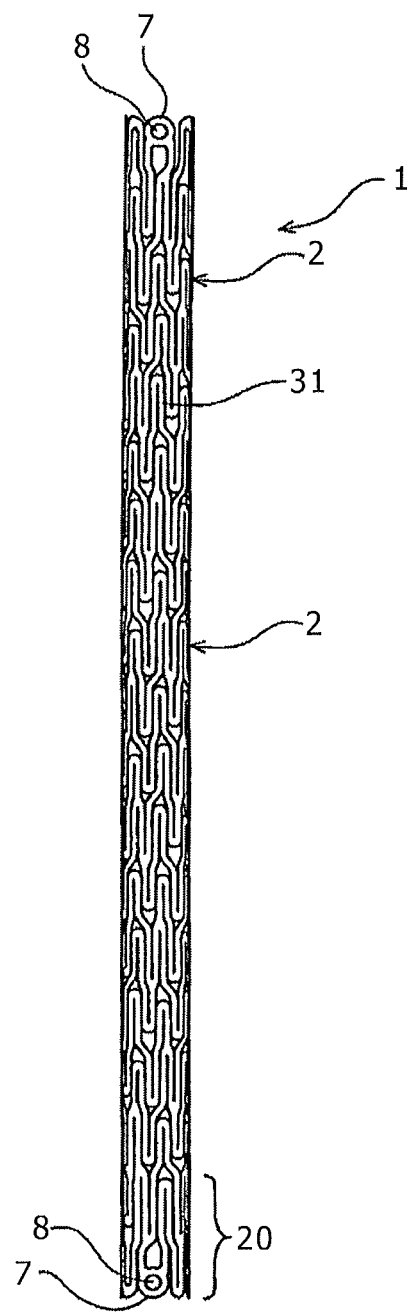
FIG. 1 is a front view of a stent according to one embodiment disclosed here.

Set forth below with reference initially to FIGS. 1-5 is a description of one embodiment of a stent disclosed here. The stent 1 disclosed here is a stent to be brought into close contact with tissue in a living body through deformation at the time of an operation of indwelling the stent in the living body.

The stent 1 includes a plurality of annular bodies (elements) 2 arrayed or arranged in an axial direction, each of the annular bodies 2 being formed in an annular shape from a linear constituent element and having a plurality of one-end-side bent sections 2a and a plurality of other-end-side bent sections 2b. In the illustrated embodiment, the one-end-side bent sections 2a are bent sections having vertices at one axial end of the annular body, and the other-end-side bent sections 2b are bent sections having vertices at the opposite axial end of the annular body. Axially adjacent annular bodies 2 are linked by link sections.

The stent 1 includes, as the link sections, at least three kinds of link sections selected from four kinds of link sections including: a vertex-vertex bent link section 31 which links a vertex of an other-end-side bent section 2b of the one-end-side annular body 2 of axially adjacent annular bodies with a vertex of an one-end-side bent section 2a of the other-endside annular body 2 of the axially adjacent annular bodies and which has at least one one-end-side bent part 3a and at least one other-end-side bent part 3b; a central part-central part bent link section 32 which links a central part 2c of a linear portion interconnecting an one-end-side bent section 2a and an other-end-side bent section 2b of the one-end-side annular body 2 of axially adjacent annular bodies with a central part 2c of a linear portion interconnecting an one-end-side bent section 2a and an other-end-side bent section 2b of the other-end-side annular body 2 of the axially adjacent annular bodies and which has at least one one-end-side bent part 3a and at least one other-end-side bent part 3b; a central part-vertex bent link section 33 which links a central part 2c of a linear portion interconnecting an one-end-side bent section 2a and an other-end-side bent section 2b of the one-end-side annular body 2 of axially adjacent annular bodies with a vertex of an one-end-side bent section 2a of the other-end-side annular body 2 of the axially adjacent annular bodies and which has at least one one-end-side bent part 3a and at least one other-end-side bent part 3b; and a vertex-central part bent link section 34 which links a vertex of an other-end-side bent section 2b of the one-end-side annular body 2 of axially adjacent annular bodies with a central part 2c of a linear portion interconnecting an one-end-side bent section 2a and an other-end-side bent section 2b of the other-end-side annular body 2 of the axially adjacent annular bodies and which has at least one one-end-side bent part 3a and at least one other-end-side bent part 3b. The at least three kinds of link sections connecting axially adjacent annular bodies include at least the vertex-vertex bent link section 31 and the central part-central part bent link section 32, and the axially adjacent annular bodies are linked by at least two different kinds of the link sections.

As above-mentioned, the stent 1 disclosed here is a stent to be brought into close contact with a tissue in a living body through deformation at the time of indwelling the stent in the living body.

The stent 1 is a so-called self-expandable stent possessing a substantially cylindrical shape, configured to be compressed radially inwardly at the time of being inserted into a living body, and to be restored to its pre-compression shape when indwelled in the living body. FIG. 1 shows the external shape of the stent 1 when compressed (when inserted into a living body). The stent is not restricted to a self-expandable stent. For example, the stent may also be a balloon-expandable stent possessing a substantially tubular body with an outer diameter permitting insertion into a lumen in a living body, and expandable when a radially spreading force is exerted on the tubular body (stent) from the inside of the tubular body.

As generally described above, the stent 1 includes a plurality of annular bodies (hereinafter referred to also as "wavy linear annular bodies") 2 arranged in the axial direction, with each of the annular bodies 2 being formed in an annular shape from a wavy-shaped linear constituent element and having a plurality of one-end-side bent sections 2a and a plurality of other-end-side bent sections 2b, with axially adjacent ones of the annular bodies 2 linked by link sections. In the illustrated embodiment, the wavy shaped linear members are each continuous.

The number of the wavy linear annular bodies 2 constituting the stent 1 is 9 in the embodiment shown by way of example in FIG. 1. Depending on the length of the stent 1, the number of the wavy linear annular bodies 2 constituting the stent 1 is preferably 3 to 90, more preferably 5 to 80.

In addition, each of the wavy linear annular bodies 2 is composed of a wavy linear body which includes the plurality of one-end-side bent sections 2a, each having a vertex, on the one end side in the axial direction of the stent 1 and the plurality of other-end-side bent sections 2b, each having a vertex, on the other (the opposite) end side in the axial direction of the stent 1, and which is in an annularly continuous endless (looped) form. The one-end-side bent sections 2a and the other-end-side bent sections 2b in the annular body 2 are alternately formed. For each wavy linear annular body, the number of one-end-side bent sections 2a and the number of other-end-side bent sections 2b are equal to each other. The number of the one-end-side bent sections and the number of the other-end-side bent sections in one wavy linear annular body 2 are each 7 (14 in total) in the embodiment shown in FIGS. 1 to 4. The number of the one-end-side bent sections, equal to the number of the other-end-side bent sections, in one wavy linear annular body 2 is preferably 4 to 15, more preferably 5 to 12.

Figure 2:
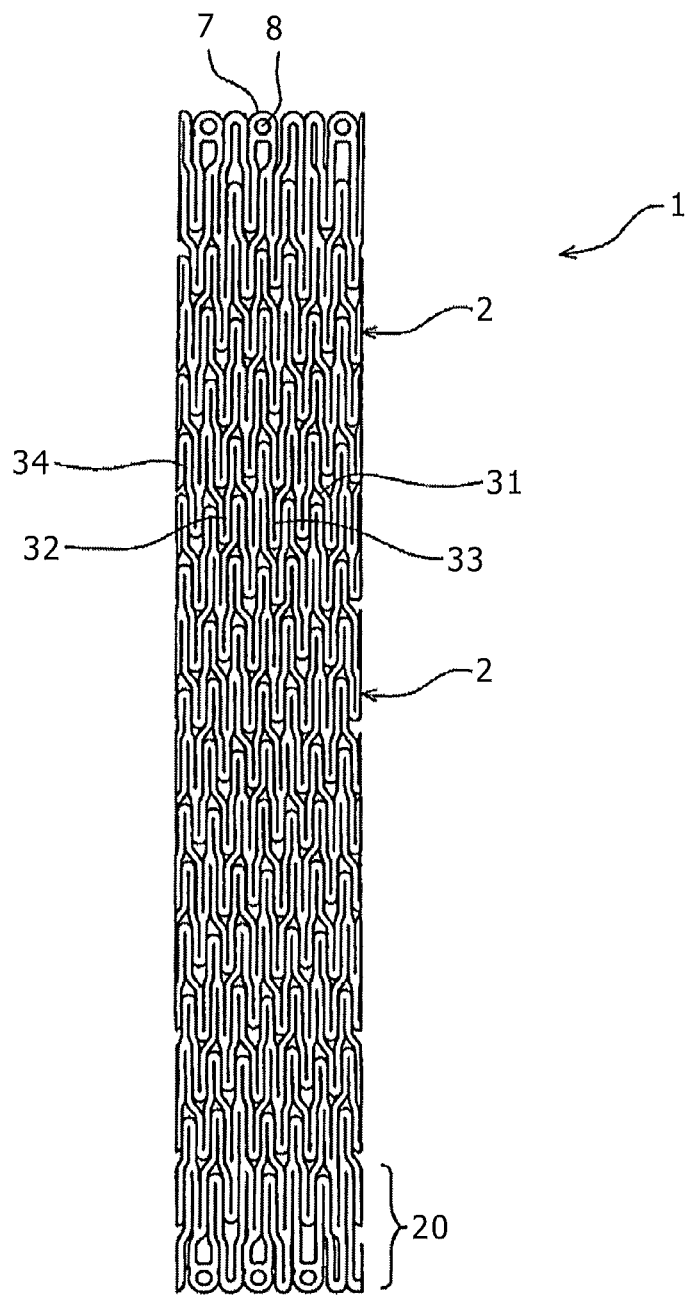
FIG. 2 is a developmental view of the stent of FIG. 1.
Figure 3:
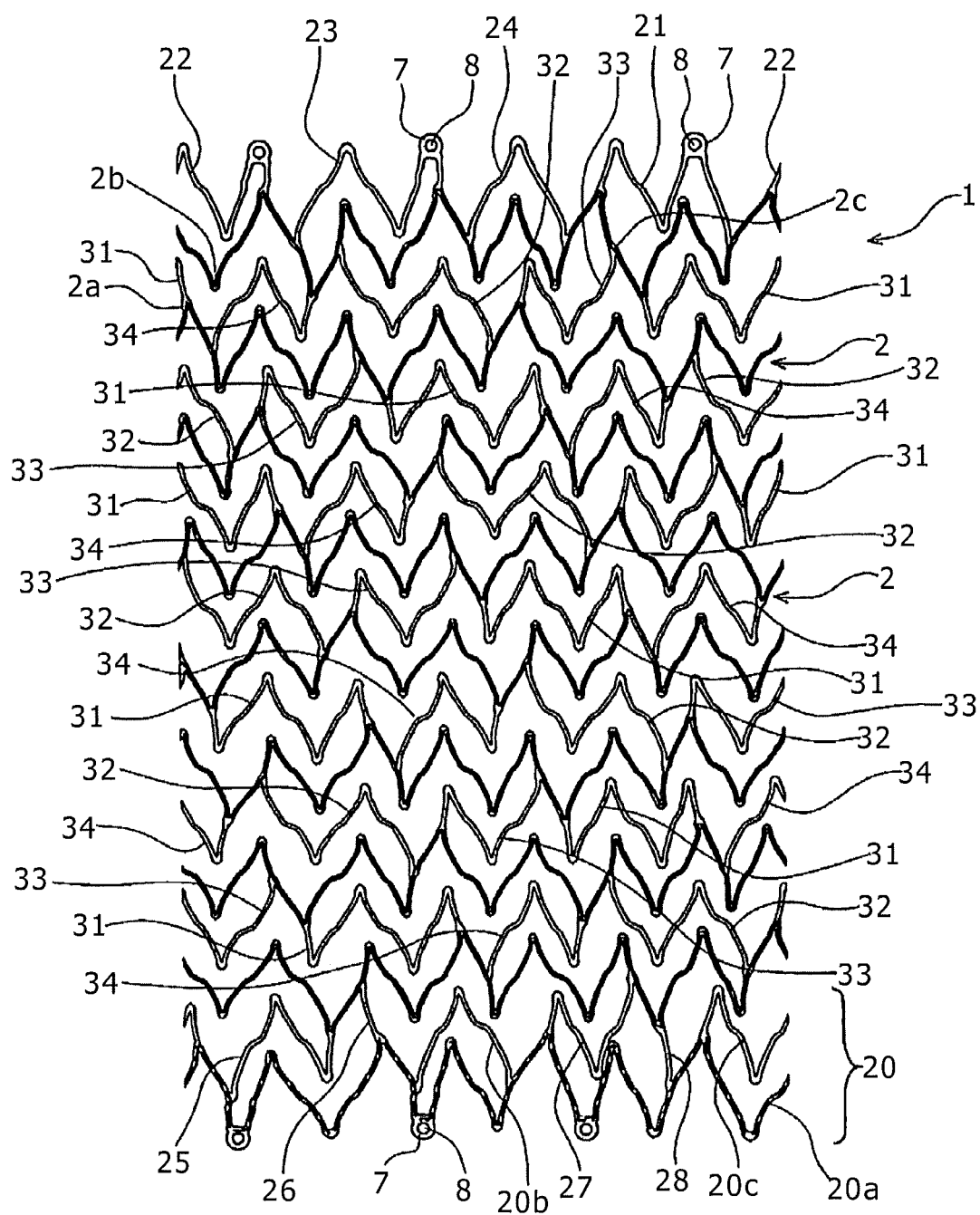
FIG. 3 is a developmental view, in an expanded state, of the stent of FIG. 1.

In the stent 1 according to the present embodiment, as shown in FIGS. 2 and 3, the annular body located at one end of the stent 1 is provided further with one-end bent linear sections 21, 22, 23 and 24 which project to one axial end side, and the one end portion of the stent 1 is composed of these one-end bent linear sections. The one-end bent linear section 21 links the vertex of one one-end-side bent section of the annular body 2 with a central part of a linear portion interconnecting another one-end-side bent section and one other-end-side bent section in the same annular body 2, and has two one-end-side bent parts and one other-end-side bent part. In addition, one of the one-end-side bent parts of the one-end bent linear section 21 is provided with a marker housing 7, which is provided with an opening section, and a contrast-medium marker 8 is fixed so as to close the opening section. The one-end bent linear section 22 links the vertex of one one-end-side bent section of the annular body 2 with the vertex of another one-end-side bent section in the same annular body 2, and has two one-end-side bent parts and one other-end-side bent part. In addition, one of the one-end-side bent parts of the one-end bent linear section 22 is provided with a maker housing 7, which is provided with an opening section, and a contrast-medium marker 8 is fixed so as to close the opening section. The one-end bent linear section 23 links a central part of a linear portion interconnecting one one-end-side bent section and one other-end-side bent section of the annular body 2 with the vertex of another one-end-side bent section in the same annular body 2, and has two one-end-side bent parts and one other-end-side bent part. In addition, one of the one-end-side bent parts of the one-end bent linear section 23 is provided with a marker housing 7, which is provided with an opening section, and a contrast-medium marker 8 is fixed so as to close the opening section. Further, the one-end bent linear section 24 links a central part of a linear portion interconnecting one one-end-side bent section and one other-end-side bent section of the annular body 2 with a central part of a linear portion interconnecting another one-end-side bent section and another other-end-side bent section in the same annular body 2, and has one one-end-side bent part.

Figure 4:
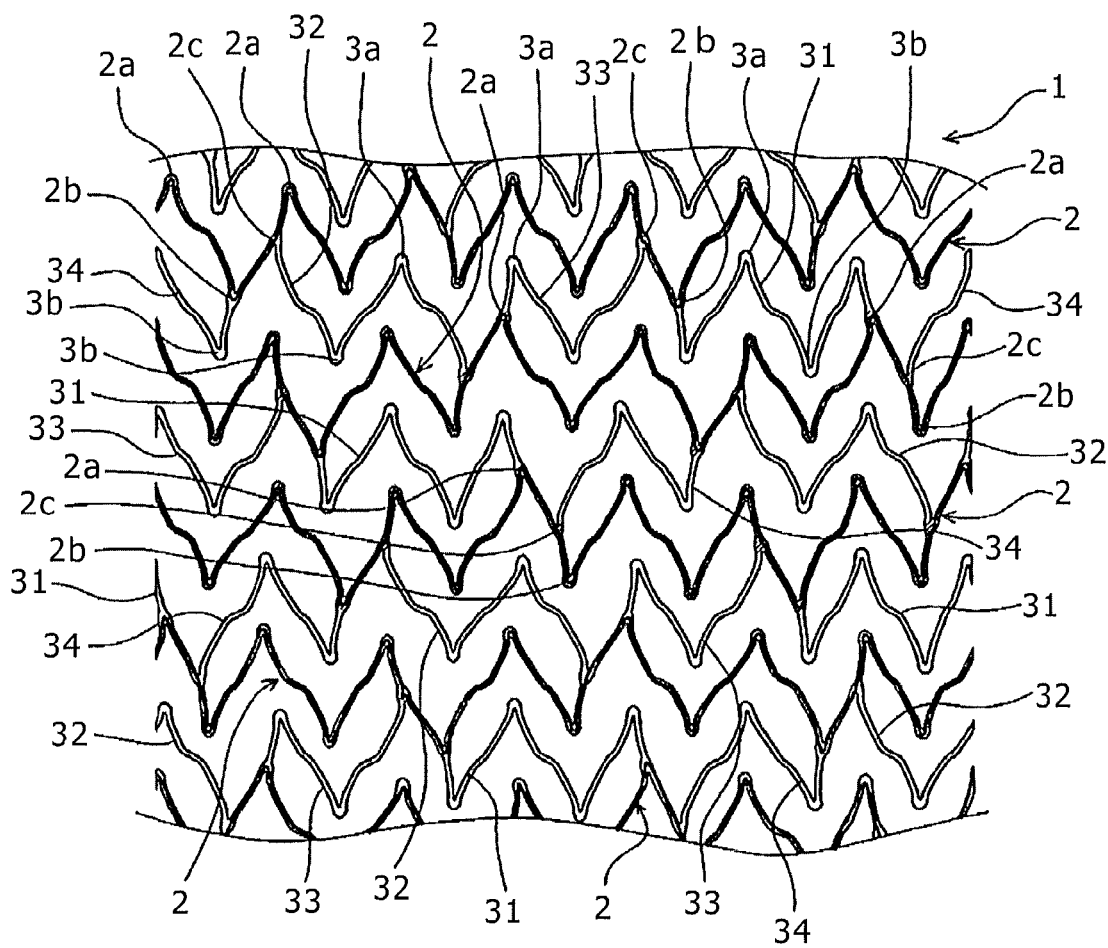
FIG. 4 is an enlarged view of a portion of the stent shown in FIG. 3.

In the stent 1 according to the present embodiment disclosed by way of example and shown in FIGS. 2, 3 and 4, every axially adjacent pair of annular bodies (all axially adjacent bodies) are linked to each other by four kinds of link sections including a vertex-vertex bent link section 31, a central part-central part bent link section 32, a central part-vertex bent link section 33, and a vertex-central part bent link section 34.

The vertex-vertex bent link section 31, as shown in FIG. 4, links the vertex of an other-end-side bent section 2b of the one-end-side annular body 2 of axially adjacent annular bodies with the vertex of an one-end-side bent section 2a of the other-end-side annular body 2 of the axially adjacent annular bodies, and has two one-end-side bent parts 3a and two other-end-side bent parts 3b. The vertex-vertex bent link section 31 thus has the two one-end-side bent parts 3a and the two other-end-side bent parts 3b, thereby being able to relatively securely impart flexibility and a rather easily compressible property to the stent 1. In addition, the vertex-vertex bent link section 31 has a larger number of bent parts and is greater in length as compared with the other link sections which will be described later (i.e., the vertex-vertex bent link section 31 possesses a great circumferential extent than the other link sections 32, 33, 34). The vertex-vertex bent link section may have only one one-end-side bent part 3a and only one other-end-side bent part 3b. The vertices of the bent sections of the annular bodies 2 in connection with the vertex-vertex bent link section 31 constitute branching parts. Further, the one-end-side bent part 3a of the vertex-vertex bent link section 31 is located between (i.e., axially overlaps with) the bent sections (specifically, between the other-end-side bent sections) of the one-end-side annular body 2 linked by this link section 31, whereas the other-end-side bent part 3b of this link section 31 is located between (i.e., axially overlaps with) the bent sections (specifically, between the one-end-side bent sections) of the other-end-side annular body 2 linked by this link section 31. Therefore, the vertex-vertex bent link section 31 imparts a relatively high expansion-retaining force to the stent 1.

The central part-central part bent link section 32, as shown in FIG. 4, links a central part 2c of a linear portion interconnecting an one-end-side bent section 2a and an other-end-side bent section 2b of the one-end-side annular body 2 of the axially adjacent annular bodies with a central part 2c of a linear portion interconnecting an one-end-side bent section 2a and an other-end-side bent section 2b of the other-end-side annular body 2 of the axially adjacent annular bodies, and has one one-end-side bent part 3a and one other-end-side bent part 3b. In addition, since the central part-central part bent link section 32 links the central parts of the linear portions in the axially adjacent annular bodies to each other, it has a certain degree of rigidity and contributes to enhancing the expansion-retaining force of the stent 1. The central part 2c is approximately a roughly middle point of the linear portion interconnecting the one-end-side bent section 2a and the other-end-side bent section 2b. The central parts 2c in the annular bodies 2 that are connected to the central part-central part bent link section 32 constitute branching parts. In addition, the central part-central part bent link section 32 is so arranged that it is not continuous with the above-mentioned vertex-vertex bent link section 31 in the circumferential direction of the stent 1. That is, the central part-central part bent link section 32 is circumferentially separated from the vertex-vertex bent link section 31 by another link section that is not one of the link sections 31, 32. In the stent according to the present embodiment, the central part-central part bent link section 32 is located substantially opposite (diametrically opposite) the vertex-vertex bent link section 31, with the center axis of the stent 1 therebetween. The central part-central part bent link section 32, preferably, has only one one-end-side bent part 3a and only one other-end-side bent part 3b. Further, the one-end-side bent part 3a of the central part-central part bent link section 32 is also located between (i.e., axially overlaps with) the bent sections (specifically, between the other-end-side bent sections) of the one-end-side annular body 2 linked by this link section 32, whereas the other-end-side bent part 3b of this link section 32 is also located between (i.e., axially overlaps with) the bent sections (specifically, between the one-end-side bent sections) of the other-end-side annular body 2 linked by this link section 32. Therefore, the central part-central part bent link section 32 imparts a high expansion-retaining force to the stent 1.

The central part-vertex bent link section 33, as shown in FIG. 4, links a central part 2c of a linear portion interconnecting an one-end-side bent section 2a and an other-end-side bent section 2b of the one-end-side annular body 2 of the axially adjacent annular bodies with the vertex of an one-end-side bent section 2a of the other-end-side annular body 2 of the axially adjacent annular bodies, and has one one-end-side bent part 3a and one other-end-side bent part 3b. In addition, since the central part-vertex bent link section 33 links the central part of the linear portion and the vertex in the axially adjacent annular bodies, it exhibits physical properties which are intermediate between those of the above-mentioned vertex-vertex bent link section 31 and those of the above-mentioned central part-central part bent link section 32. The central part-vertex bent link section 33 is so arranged that it is located between the vertex-vertex bent link section 31 and the central part-central part bent link section 32 in the circumferential direction of the stent 1. The central part 2c and the vertex of the bent section 2a in the annular bodies 2 in connection with this bent link section 33 each constitute branching parts. The central part-vertex bent link section 33, preferably, has only one one-end-side bent part 3a and only one other-end-side bent part 3b. Further, the one-end-side bent part 3a of the central part-vertex bent link section 33 is also located between (i.e., axially overlaps with) the bent sections (specifically, between the other-end-side bent sections) of the one-end-side annular body 2 linked by this link section 33, whereas the other-end-side bent part 3b of this link section 33 is also located between (i.e., axially overlaps with) the bent sections (specifically, between the one-end-side bent sections) of the other-end-side annular body 2 linked by this link section 33. Accordingly, the central part-vertex bent link section 33 imparts a relatively high expansion-retaining force to the stent 1.

The vertex-central part bent link section 34, as shown in FIG. 4, links the vertex of an other-end-side bent section 2b of the one-end-side annular body 2 of the axially adjacent annular bodies with a central part 2c of a linear portion interconnecting an one-end-side bent section 2a and an other-end-side bent section 2b of the other-end-side annular body 2 of the axially adjacent annular bodies, and has one one-end-side bent part 3a and one other-end-side bent part 3b. In addition, since the vertex-central part bent link section 34 links the central part of the linear portion and the vertex in the axially adjacent annular bodies, it exhibits physical properties which are intermediate between those of the above-mentioned vertex-vertex bent link section 31 and those of the above-mentioned central part-central part bent link section 32. The vertex-central part bent link section 34 is so arranged that it is located between the vertex-vertex bent link section 31 and the central part-central part bent link section 32 in the circumferential direction of the stent. In addition, in the stent 1 according to the present embodiment, the vertex-central part bent link section 34 is located substantially opposite (diametrically opposite) the above-mentioned central part-vertex bent link section 33, with the center axis of the stent 1 therebetween. The central part 2c and the vertex of the bent section 2b in the annular bodies 2 in connection with this bent link section 34 each constitute branching parts. The vertex-central part bent link section 34, preferably, has only one one-end-side bent part 3a and only one other-end-side bent part 3b. Further, the one-end-side bent part 3a of the vertex-central part bent link section 34 is also located between (i.e., axially overlaps with) the bent sections (specifically, between the other-end-side bent sections) of the one-end-side annular body 2 linked by this link section 34, whereas the other-end-side bent part 3b of this link section 34 is also located between (i.e., axially overlaps with) the bent sections (specifically, between the other-end-side bent sections) of the other-end-side annular body 2 linked by this link section 34. Therefore, the vertex-central part bent link section 34 imparts a relatively high expansion-retaining force to the stent 1.

In addition, the link sections between axially adjacent annular bodies are so arranged that, as viewed in the circumferential direction, on the left side of the vertex-vertex bent link section 31 is located the central part-vertex bent link section 33, on the left side of which is located the central part-central part bent link section 32, on the left side of which is located the vertex-central part bent link section 34, on the left side of which is located the vertex-vertex bent link section 31, and, therefore, the vertex-vertex bent link section 31, the central part-vertex bent link section 33, the central part-central part bent link section 32 and the vertex-central part bent link section 34 are arranged in an annular pattern and in this order along the left-hand circumferential direction.

In the stent 1 according to the present embodiment, as shown in FIGS. 2 and 3, an other-end annular section 20a is disposed at the other end portion 20 of the stent 1. The annular section 20a is a wavy linear annular body having seven one-end-side bent sections and seven other-end-side bent sections, like the above-mentioned annular bodies 2. In addition, some of the seven other-end-side bent sections of the other-end annular section 20a (specifically, three bent sections) are each provided with a marker housing 7, each possessing an opening section, and a contrast-medium marker 8 is fixed so as to close the opening section.

The other-end annular section 20a and the adjacent annular body 2 are linked to each other by a plurality of other-end link sections. In the stent 1 according to the present embodiment, other-end link sections 25, 26, 27 and 28 are provided between the other-end annular section 20a and the adjacent annular body 2. The other-end link section 25 links the vertex of an other-end-side bent section 2b of the annular body 2 with a central part of a linear portion interconnecting an one-end-side bent section and an other-end-side bent section of the other-end annular section 20a, and has one one-end-side bent part and one other-end-side bent part. The other-end link section 26 links a central part of a linear portion interconnecting an one-end-side bent section and an other-end-side bent section of the annular body 2 with the vertex of an one-end-side bent section of the other-end annular section 20a, and has a rectilinear shape with no bent part. The other-end link section 27 links a central part of a linear portion interconnecting an one-end-side bent section and an other-end-side bent section of the annular body 2 with the vertex of an one-end-side bent section of the other-end annular section 20a, and has one one-end-side bent part and one other-end-side bent part. The other-end link section 28 links the vertex of an other-end-side bent section of the annular body 2 with a central part of a linear portion interconnecting an one-end-side bent section and an other-end-side bent section of the other-end annular section 20a, and has a rectilinear shape with no bent part.

Further, as shown in FIG. 3, the other-end annular section 20a is provided with reinforcing bent linear sections 20b and 20c each having a starting end and a terminal end which are both linked to the other-end annular section 20a. The reinforcing bent linear section 20b links central parts of linear portions each interconnecting an one-end-side bent section and an other-end-side bent section of the other-end annular section 20a, and has one one-end-side bent part. The reinforcing bent linear section 20c links the vertexes of adjacent one-end-side bent sections of the other-end annular section 20a, and has two one-end-side bent parts and one other-end-side bent part. The above-described configuration helps impart a relatively high shape-retaining property to the other end portion of the stent 1.

In addition, in the stent 1 according to the present embodiment, the above-mentioned vertex-vertex bent link sections 31 are arranged in a spiral pattern with respect to the axial direction of the stent. That is, each axially successive vertex-vertex bent link section 31 is circumferentially offset from the axially preceding vertex-vertex bent link sections 31. Similarly, the central part-central part bent link sections 32 are also arranged in a spiral pattern with respect to the axial direction of the stent 1. That is, each axially successive central part-central part bent link sections 32 is circumferentially offset from the axially preceding central part-central part bent link section 32. Therefore, neither the vertex-vertex bent link sections 31 nor the central part-central part bent link sections 32 are continuously arranged on a straight line in the axial direction of the stent 1. Similarly, the central part-vertex bent link sections 33 and the vertex-central part bent link sections 34 are also arranged respectively in spiral patterns with respect to the axial direction of the stent 1. Thus, in the stent 1 according to the present embodiment, the link sections of the same kind are not continuously arranged on a straight line in the axial direction of the stent.

The above-mentioned contrast-medium marker 8 is fixed so as to close the opening section. The contrast-medium marker 8 is preferably fixed, for example, by a method in which a disk-shaped member of a contrast material (contrast medium) having a slightly smaller portion and a slightly larger portion as compared with the opening section formed in the marker housing 7 is disposed in the opening section and is caulked in a rivet-like form by pressing from both sides thereof.

The contrast-medium marker may be any one of a radiopaque marker, an ultrasonic contrast marker and the like. The marker is formed of any one of a radiopaque material, an ultrasonically non-transmitting material and the like. Preferable examples of the material for forming the marker include gold, platinum, tungsten, tantalum, iridium, palladium, gold-palladium alloy, platinum-iridium alloy, NiTiPd alloy, and NiTiAu alloy.

Figure 5:
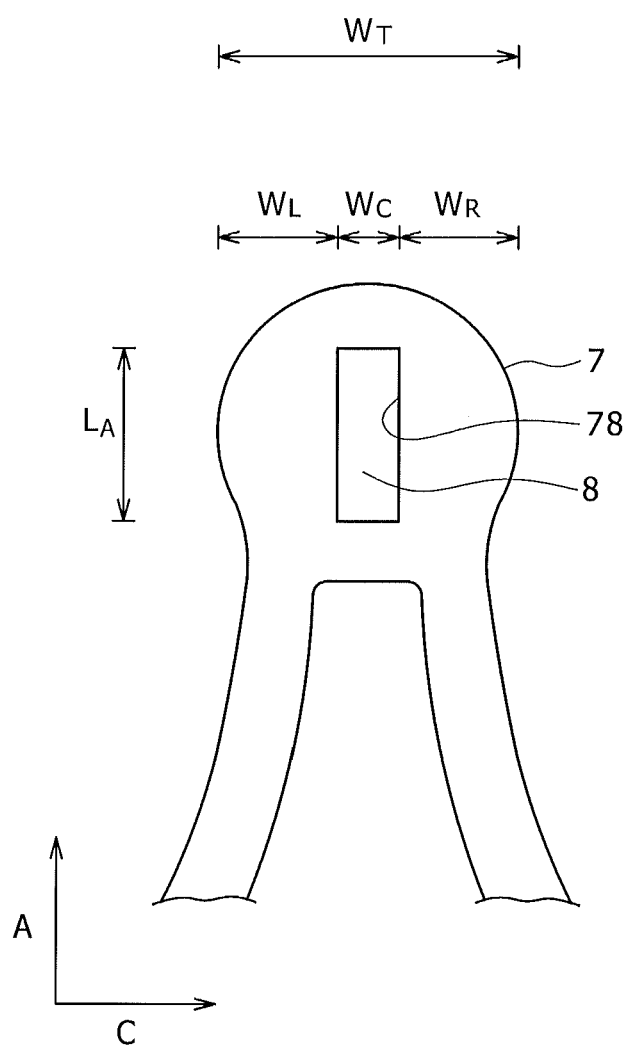
FIG. 5 is an enlarged view of a part of the stent shown in FIG. 3 including an example of a marker housing and an opening section.

In addition, the marker housing and the opening section may be as shown in FIG. 5. An opening section 78 shown in FIG. 5 has a structure in which the width (length) WC along the circumferential direction C orthogonal to the axial direction A of the stent is not more than ⅓ times the width (length) WT of the marker housing 7 along the circumferential direction C. Therefore, at the time of containing the stent in a distal portion of a stent-containing tubular member (described later) and at the time of releasing the stent from the distal portion of the stent-containing tubular member, it is possible to restrain the marker housing 7 from interfering with the stent-containing tubular member, specifically, it is possible to restrain the marker housing 7 from being caught on the inner surface of the stent-containing tubular member. In other words, in spite of the presence of the opening section 78, the stent can be contained in the distal portion of the stent-containing tubular member and be released from the distal portion of the stent-containing tubular member, while maintaining the curvature of the marker housing 7, so that resistance during these operations is reduced.

The opening section 78 is rectangular in shape, and its length LA along the axial direction A of the stent is greater than its width WC, which makes it possible to secure the area of the opening section 78 (the area of the contrast-medium marker 8) and to maintain the contrast property (radiopacity or non-transmitting property) of the contrast-medium marker 8.

With respect to the circumferential direction C of the stent, the respective widths (lengths) WL and WR of the portions located on both sides of the opening section 78 are greater than the width (length) WC of the opening section 78, and the opening section 78 is located in a central area of the marker housing 7. Therefore, it is possible to efficiently maintain the curvature of the marker housing 7, and to efficiently restrain the marker housing 7 from interfering with the stent-containing tubular member.

Figure 6:
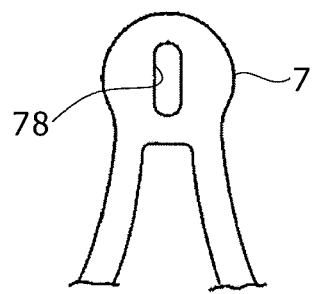
FIG. 6 is an enlarged view of another embodiment of the marker housing and the opening section.
Figure 7:
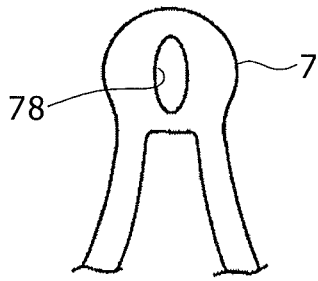
FIG. 7 is an enlarged view of a further embodiment of the marker housing and the opening section.
Figure 8:
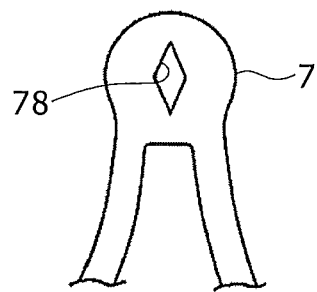
FIG. 8 is an enlarged view of yet another embodiment of the marker housing and the opening section.

The shape of the opening section 78 is not restricted to a rectangle; for example, a round-ended rectangle (FIG. 6), an ellipse (FIG. 7), and a rhombus (FIG. 8) may also be adopted.

Figure 9:
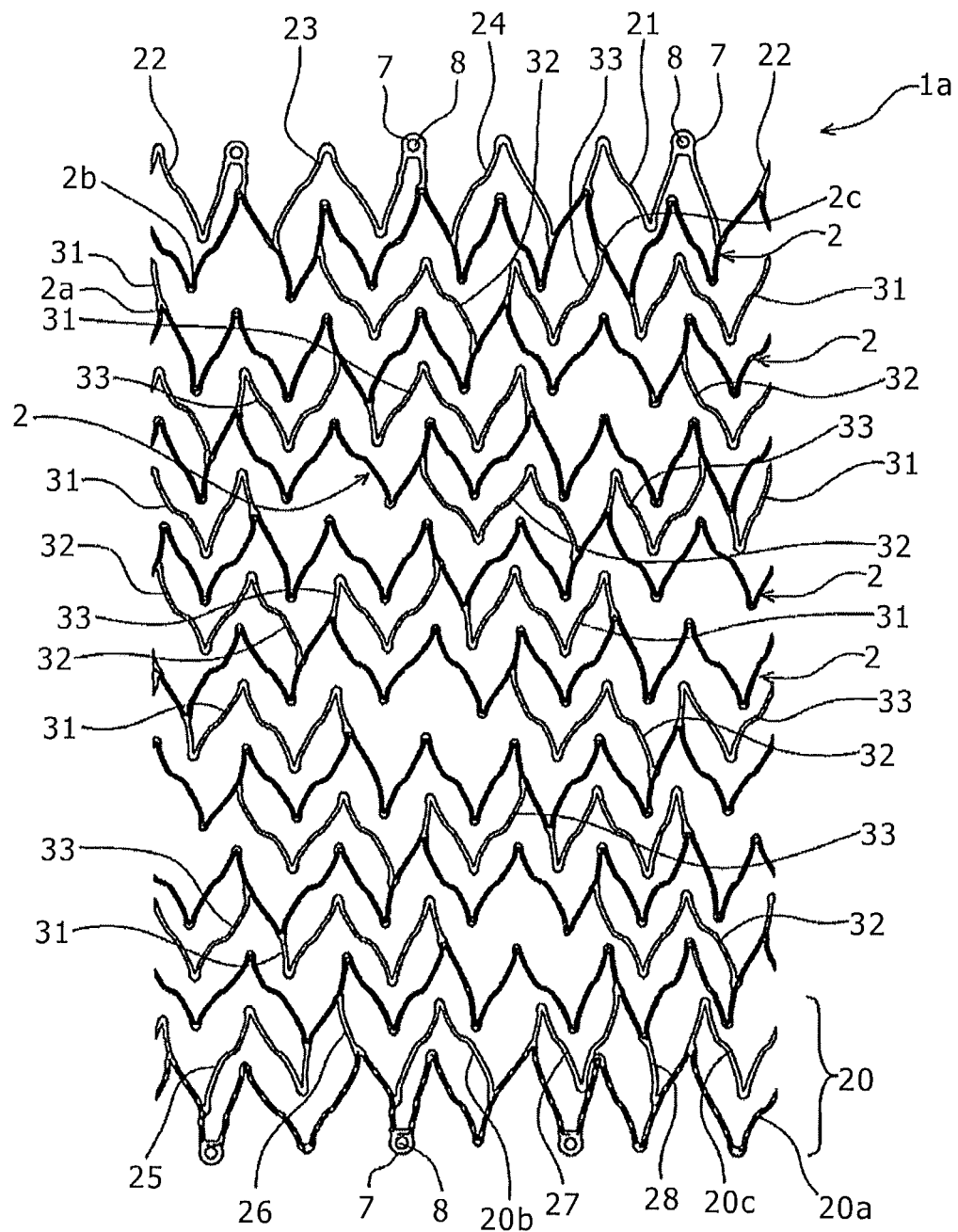
FIG. 9 is a developmental view of a stent, in an expanded state, according to another embodiment.
Figure 10:
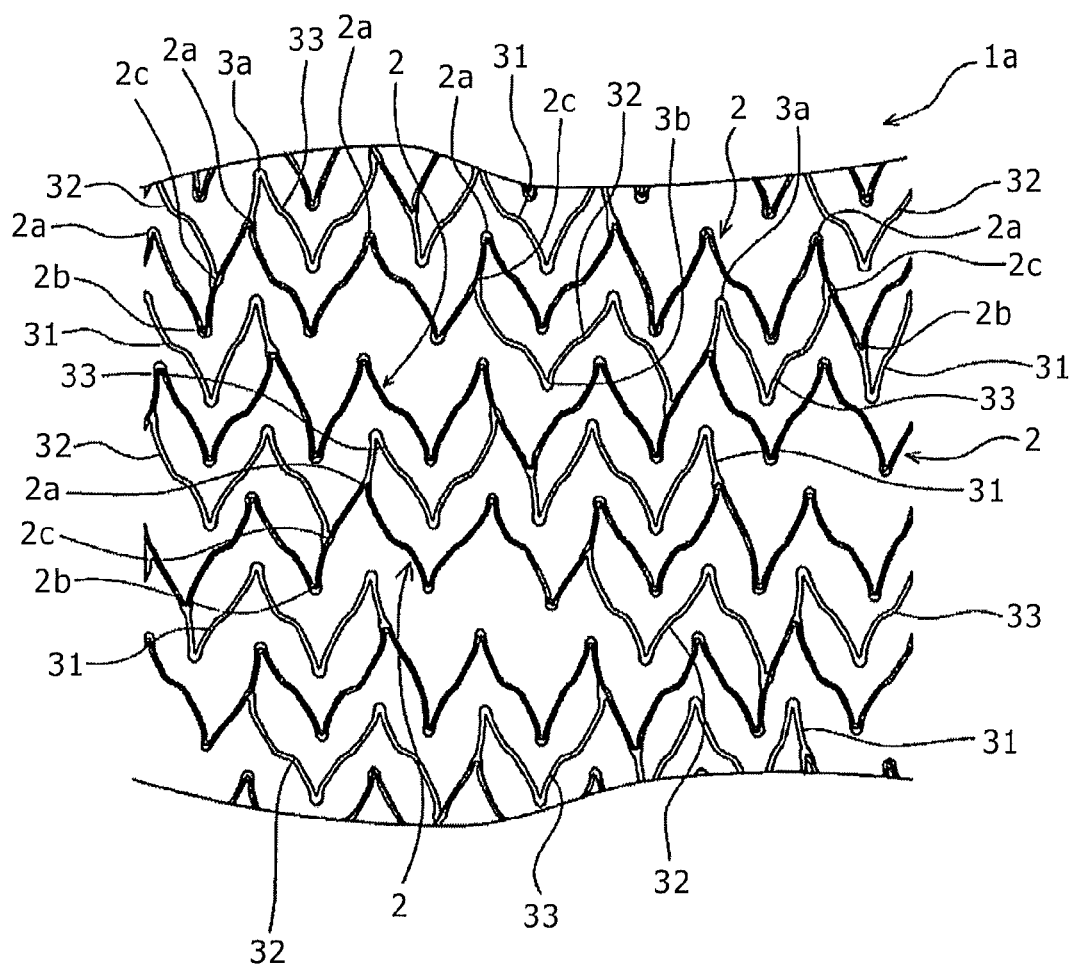
FIG. 10 is an enlarged view of a portion of the stent shown in FIG. 9.

The stent may also be a stent 1a as shown in FIGS. 9 and 10. As shown in FIGS. 9 and 10, the stent 1a in the present embodiment is of the type in which every axially adjacent pair of annular bodies (all axially adjacent bodies) are linked to each other by three kinds of link sections including the vertex-vertex bent link section 31, the central part-central part bent link section 32, and either the central part-vertex bent link section 33 or the vertex-central part bent link section 34. Specifically, every axially adjacent pair of annular bodies (all axially adjacent bodies) are linked by at least the vertex-vertex bent link section 31, the central part-central part bent link section 32, and the central part-vertex bent link section 33. The difference between the above-described stent 1 and the present stent 1a lies only in that the present stent 1a does not have the vertex-central part bent link section 34 (at the right next to the vertex-vertex bent link section 31), with the other points being the same as in the above-described stent 1. In addition, the stent 1a has void areas where no link section is provided between the adjacent annular bodies. Due to the presence of the void areas, the stent 1a has a relatively high flexibility although it is lowered in the expansion-retaining force. The void areas (link section-lacking areas) are arranged in a spiral pattern with respect to the axial direction of the stent 1a; thus, the void areas are not continuously arranged on a straight line in the axial direction of the stent.

Figure 11:
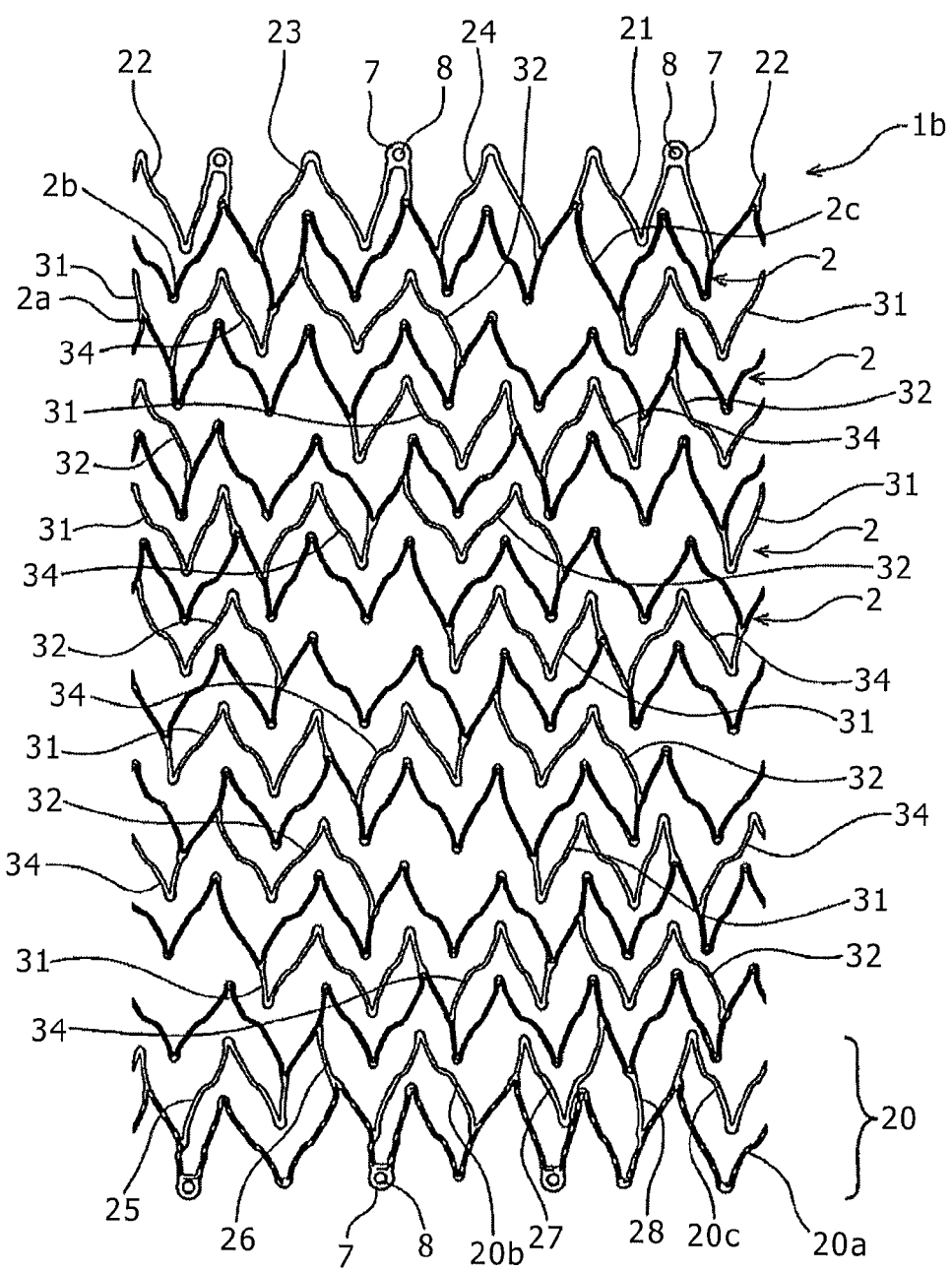
FIG. 11 is a developmental view of a stent, in an expanded state, according to a further embodiment.
Figure 12:
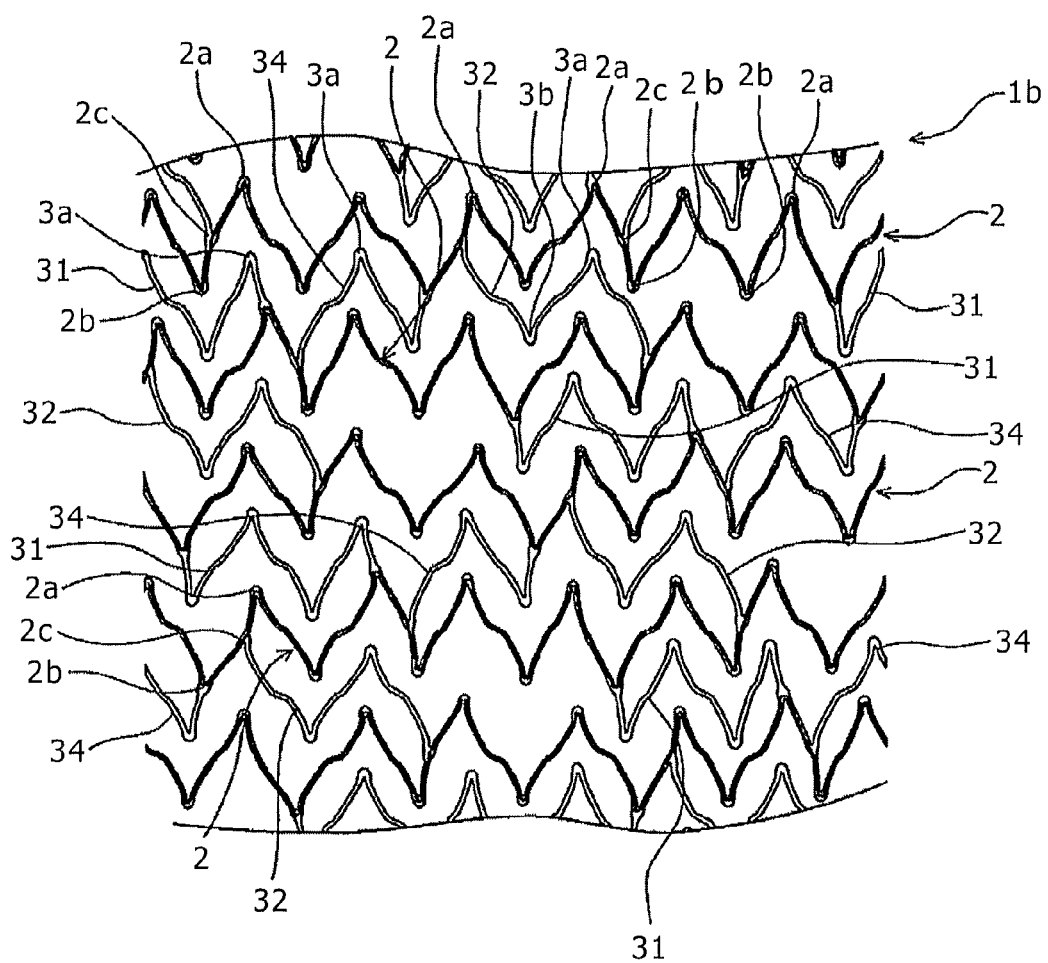
FIG. 12 is an enlarged view of a portion of the stent shown in FIG. 11.

The stent may also be a stent 1b as shown in FIGS. 11 and 12. As shown in FIGS. 11 and 12, the stent 1b according to the present embodiment is of the type in which every axially adjacent pair of annular bodies (all axially adjacent bodies) are linked to each other by three kinds of link sections including the vertex-vertex bent link section 31, the central part-central part bent link section 32, and either the central part-vertex bent link section 33 or the vertex-central part bent link section 34. Specifically, every axially adjacent pair of annular bodies (all axially adjacent bodies) are linked by at least the vertex-vertex bent link section 31, the central part-central part bent link section 32, and the vertex-central part bent link section 34. The difference between the above-described stent 1 and the present stent 1b resides only in that the present stent 1b does not have the central part-vertex bent link section 33 (at the left next to the vertex-vertex bent link section 31), with the other points being the same as in the above-described stent 1. In addition, the stent 1b has void areas where no link section is provided between the axially adjacent annular bodies. Due to the presence of the void areas, the stent 1b has a relatively high flexibility although it is lowered in the expansion-retaining force. The void areas (link section-lacking areas) are arranged in a spiral pattern with respect to the axial direction of the stent 1b; thus, the void areas are not continuously arranged on a straight line in the axial direction of the stent.

Figure 13:
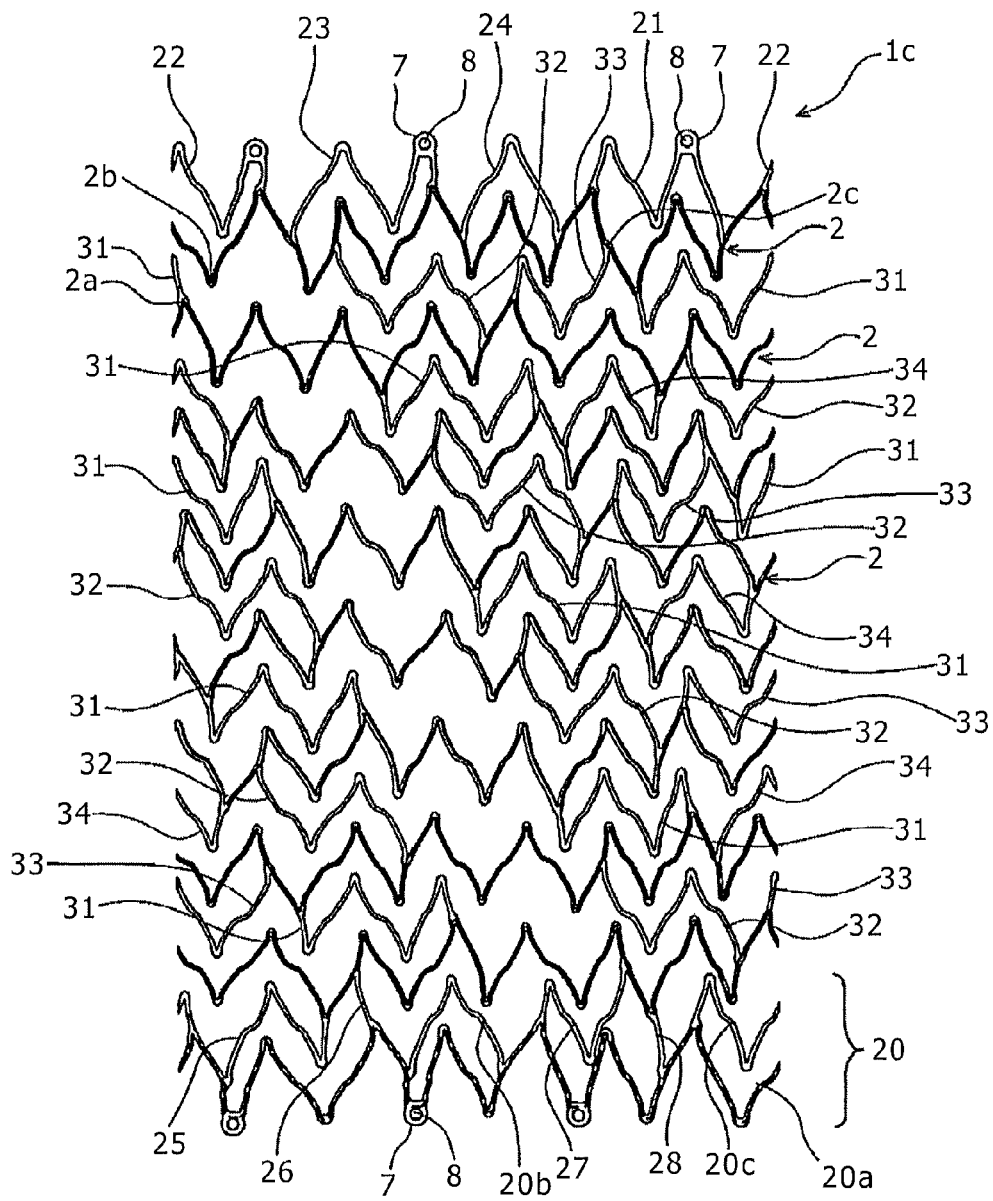
FIG. 13 is a developmental view of a stent, in an expanded state, according to yet another embodiment.
Figure 14:
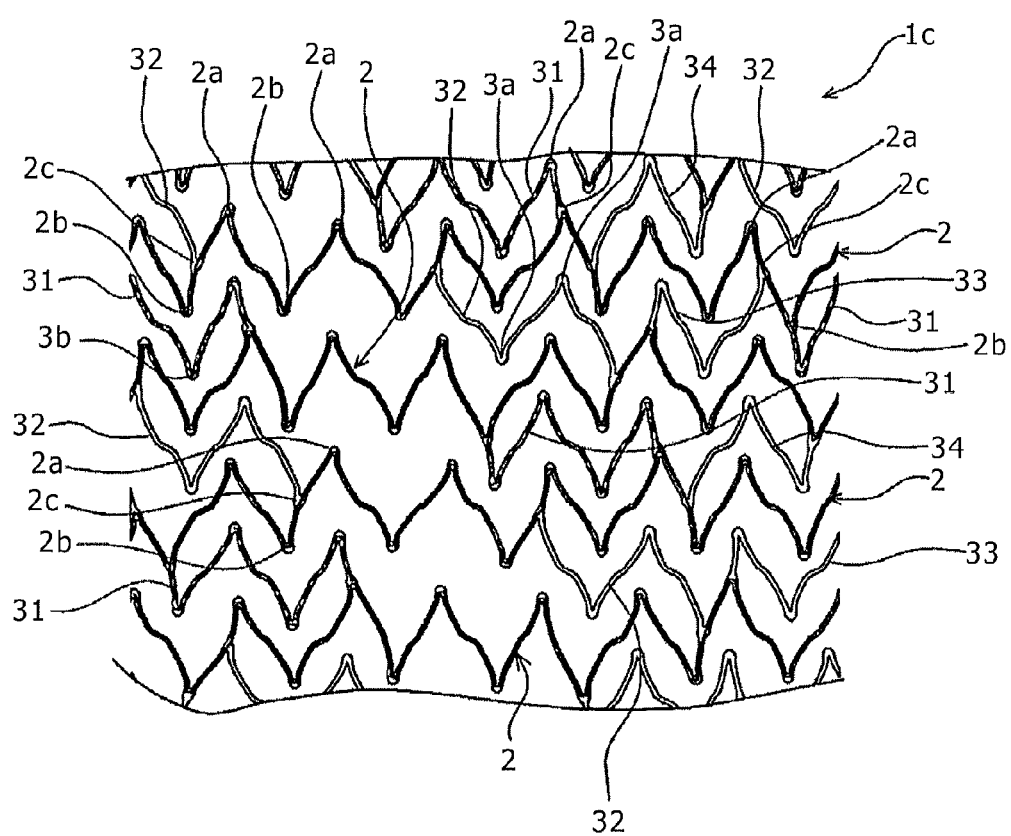
FIG. 14 is an enlarged view of a portion of the stent shown in FIG. 13.

In addition, the stent may also be a stent 1c as shown in FIGS. 13 and 14. As shown in FIGS. 13 and 14, the stent 1c according to the present embodiment is of the type in which every axially adjacent pair of annular bodies (all axially adjacent bodies) are linked to each other by three kinds of link sections including the vertex-vertex bent link section 31, the central part-central part bent link section 32, and either the central part-vertex bent link section 33 or the vertex-central part bent link section 34. Specifically, a form wherein the axially adjacent pair of annular bodies are linked by the vertex-vertex bent link section 31, the central part-central part bent link section 32, and the central part-vertex bent link section 33 and a form wherein the axially adjacent pair of annular bodies are linked by the vertex-vertex bent link section 31, the central part-central part bent link section 32, and the vertex-central part bent link section 34 are alternately arranged along the axial direction of the stent. The difference between the above-described stent 1 and the present stent 1c lies only in that, in the present stent 1c, the vertex-central part bent link section 34 (at the right next to the vertex-vertex bent link section 31) and the central part-vertex bent link section 33 (at the left next to the vertex-vertex bent link section 31) are omitted alternately along the axial direction of the stent from one end side toward the other end side of the stent, with the other points being the same as in the above-described stent 1. The stent 1c also has void areas where no link section is provided between the axially adjacent annular bodies. Due to the presence of the void areas, the stent 1c has a relatively high flexibility although it is lowered in the expansion-retaining force. In addition, the void areas (link section-lacking areas) are arranged obliquely with respect to the axial direction of the stent 1c, thus, the void areas are not continuously arranged on a straight line in the axial direction of the stent.

Figure 15:
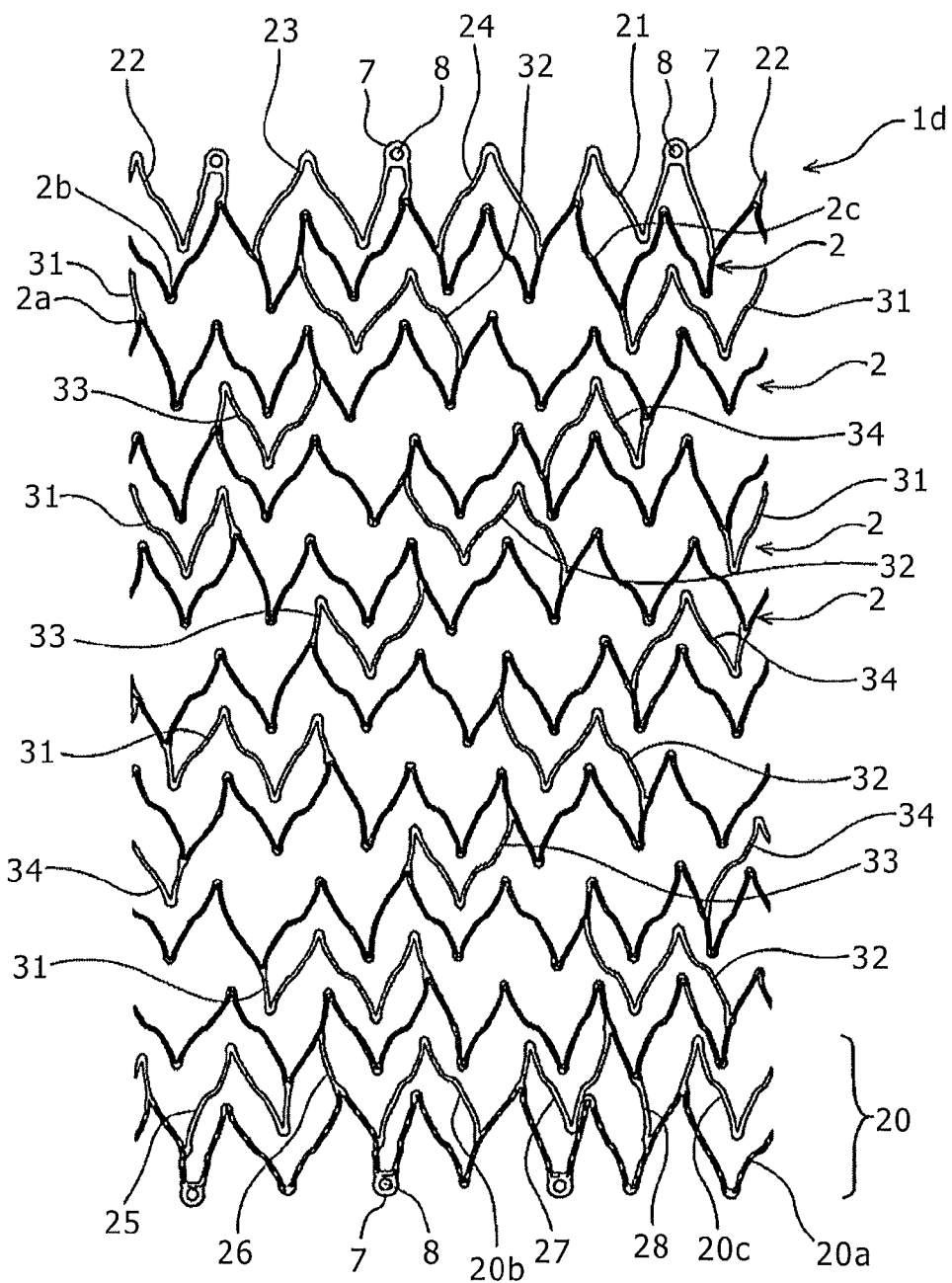
FIG. 15 is a developmental view of a stent, in an expanded state, according to a yet further embodiment.
Figure 16:
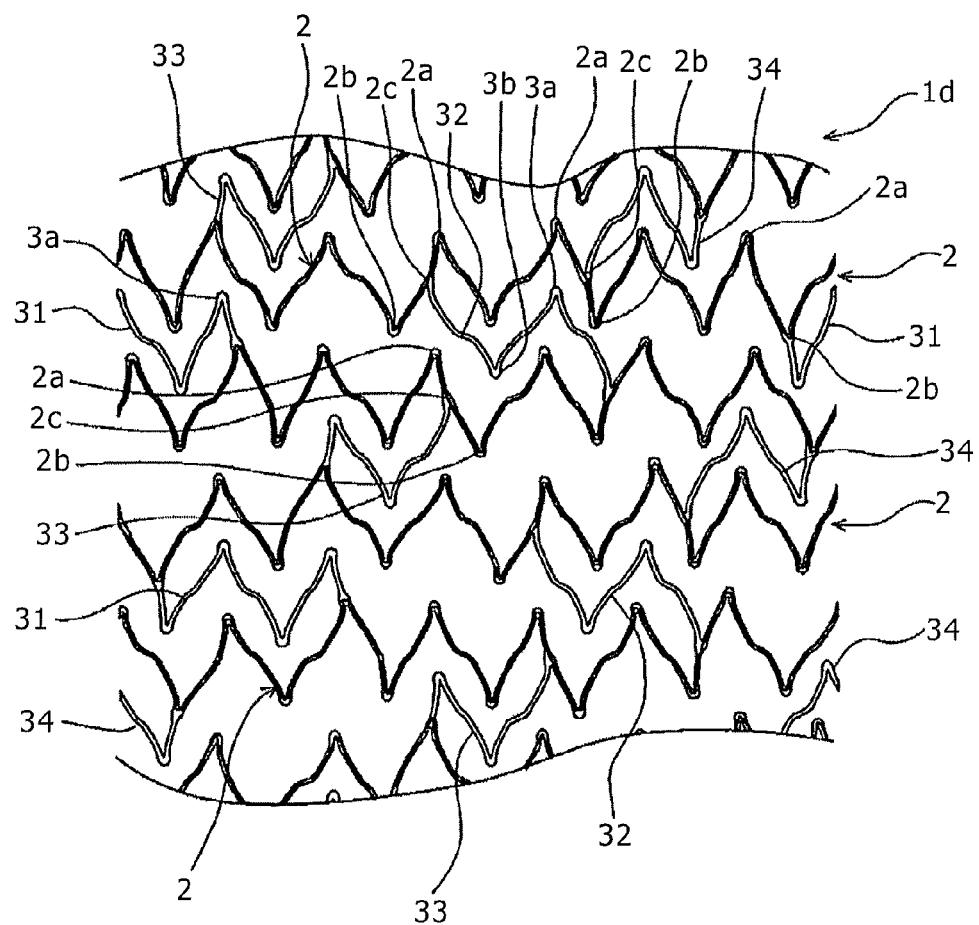
FIG. 16 is an enlarged view of a portion of the stent shown in FIG. 15.

The stent may also be a stent 1d as shown in FIGS. 15 and 16. As shown in FIGS. 15 and 16, in the stent 1d according to the present embodiment, a first linkage form wherein the axially adjacent pair of annular bodies are linked by the vertex-vertex bent link section 31 and the central part-central part bent link section 32 and a second linkage form wherein the axially adjacent pair of annular bodies are linked by the central part-vertex bent link section 33 and the vertex-central part bent link section 34 are alternately arranged along the axial direction of the stent. Every axially adjacent pair of the annular bodies (all axially adjacent bodies) are linked by two kinds of link sections, and the link sections adjacent to each other in the axial direction of the stent are different in the type of the two kinds of link sections. The difference between the above-described stent 1 and the present stent 1d resides only in that, in the present stent 1d, an axially adjacent pair of annular bodies lacking the central part-vertex bent link section 33 and the vertex-central part bent link section 34 and an axially adjacent pair of annular bodies lacking the vertex-vertex bent link section 31 and the central part-central part bent link section 32 are arranged alternately along the axial direction of the stent from one end side toward the other end side of the stent, with the other points being the same as in the above-described stent 1. In addition, the stent 1d also has void areas where no link section is provided between the axially adjacent annular bodies. Due to the presence of the void areas, the stent 1d has a relatively high flexibility although it is lowered in the expansion-retaining force. The void areas (link section-lacking areas) are arranged in a disperse manner with respect to the axial direction of the stent 1d.

In the stents according to all the above-described embodiments, the diameter of the stent when non-expanded (or when compressed) is preferably 0.8 to 1.8 mm, and more preferably 0.9 to 1.4 mm. The length of the stent when non-expanded (or when compressed) is preferably 9 to 200 mm. The length of one annular body is preferably 0.7 to 2.0 mm. The diameter of the stent at the time of formation (before compression) is preferably 1.5 to 5.5 mm, and more preferably 2.0 to 5.0 mm. The material thickness of the stent is preferably 0.05 to 0.15 mm, and more preferably 0.08 to 0.12 mm. The width of the linear constituent element is preferably 0.07 to 0.15 mm, and more preferably 0.08 to 0.13 mm.

In addition, as a material which can be employed in the case of the stent being a self-expandable stent, superelastic metals are used suitably. As the superelastic metals, superelastic alloys are used preferably. The term "superelastic alloys" used here means alloys which are generally called shape memory alloys and which show superelasticity at least at a living body temperature (around 37° C.). More preferably, such superelastic alloys as Ti—Ni alloys containing 49 to 53 atomic % of Ni, Cu—Zn alloys containing 38.5 to 41.5 wt % of Zn, Cu—Zn—X alloys (X=Be, Si, Sn, Al, or Ga) containing 1 to 10 wt % of X, and Ni—Al alloys containing 36 to 38 atomic % of Al are used. Especially preferable are the above-mentioned Ti—Ni alloys. Mechanical characteristics of the above-mentioned alloys can be appropriately changed by adopting Ti—Ni—X alloys (X=Co, Fe, Mn, Cr, V, Al, Nb, W, B or the like) obtained by replacing a part of the Ti—Ni alloys with 0.01 to 10.0 wt % of X, or adopting Ti—Ni—X alloys (X=Cu, Pb, Zr) obtained by replacing a part of the Ti—Ni alloys with 0.01 to 30.0 atomic % of X, or by selection of cold work ratios or/and final heat treatment conditions. Further, the above-mentioned Ti—Ni—X alloys can be used after appropriately changing their mechanical characteristics through selection of cold work ratios or/and final heat treatment conditions. The buckling strength (yield stress when load is applied) of the superelastic alloy to be used is 5 to 200 kg/mm2 (22° C.), preferably 8 to 150 kg/mm2, and the restoring stress (yield stress when load is eliminated) of the superelastic alloy is 3 to 180 kg/mm2 (22° C.), preferably 5 to 130 kg/mm2. The term "superelasticity" used here means a property of a material such that even after deformation (bending, stretching, or compression) of the material into a region in which ordinary metal is plastically deformed at a service temperature, release of the deformation results in the material being restored substantially to its pre-deformation shape without need for heating.

Examples of the material for the stent in the case of the stent being a balloon-expandable stent include stainless steel, tantalum, tantalum alloys, platinum, platinum alloys, gold, gold alloys, and cobalt-based alloys such as cobalt-chromium alloy. The material may be plated with noble metal (gold, platinum) after formed into a stent shape. As the stainless steel, preferred is SUS316L, which is the highest of stainless steels in corrosion resistance.

In addition, the stent is preferably chamfered. Chamfering of the stent can be performed by a method in which after the stent is formed into the final shape, the stent is subjected to chemical polishing, electrolytic polishing or mechanical polishing.

Further, after the stent in the final shape is produced, the stent is preferably annealed. Annealing enhances the flexibility and trackability of the stent as a whole, and helps ensure improved indwelling properties in a bent blood vessel. When the stent is annealed, the force for restoring to the pre-expansion shape after expansion of the stent, particularly, that force for returning into a rectilinear shape which is exhibited when the stent is expanded in a bent blood vessel is reduced, so that the physical stimulus given to the inner surface of the bent blood vessel is reduced, whereby the risk of restenosis can be lessened, as compared with the case where the annealing is not conducted. In order that an oxide film is not formed on the surface of the stent, the annealing is preferably conducted by heating the stent to a temperature of 900 to 1200° C. in an inert gas atmosphere (for example, mixed gas of nitrogen and hydrogen), followed by slow cooling.

Now, a stent delivery system (living organ dilating instrument) according to embodiments disclosed by way of example is described below, referring to embodiments shown beginning with FIG. 17.

The stent delivery system 310 includes a stent-containing tubular member 305, the above-described stent 1 contained in a distal portion (tip portion) of the stent-containing tubular member 305, and a releasing mechanism which is slidably passed inside the stent-containing tubular member 305 so as to release the stent 1 via the distal end (tip) of the stent-containing tubular member 305.

More specifically, the stent delivery system 310 includes: a distal-side tube 312 having a guide wire lumen 321; a proximal-side tube 314, a fixing tube 318 to which a proximal portion of the distal-side tube 312 and a distal portion of the proximal-side tube 314 are fixed and which has an opening 323 communicating with the guide wire lumen 321; a stent-containing tubular member 305 which encloses the distal side of the distal-side tube 312 and which can be slid toward the proximal end of the distal-side tube 312; the stent 1 contained in the stent-containing tubular member 305; and pulling wires 306 (306a, 306b) each of which has one end section fixed to the stent-containing tubular member 305, extends inside the proximal-side tube 314 and constitutes moving means for moving the stent-containing tubular member 305 toward the proximal side by pulling the pulling wires 306 (306a, 306b) toward the side of the proximal end of the proximal-side tube 314.

In addition, the distal-side tube 312 has a stent proximal end lock section 322 which is located on the distal side of the distal-side tube 312, abuts on the proximal end of the stent 1 contained in the stent-containing tubular member 305, and restricts movement of the stent 1 toward the proximal side.

The stent 1 is formed in a substantially cylindrical shape, is contained in the stent-containing tubular member 305 in the state of being compressed toward the center axis of the stent (compressed radially), and is restored to its pre-compressing shape through outward expansion when released from the stent-containing tubular member 305.

The stent delivery system 310 has a slide tube 317 disposed to be proximate to the proximal end of the stent-containing tubular member 305. The slide tube 317 can be contained in the fixing tube 318, or the slide tube 317 can be fitted over the fixing tube 318. The slide tube 317 can be moved toward the proximal side (in the proximal direction) together with the stent-containing tubular member 305 by pulling of the pulling wire 306 (306a, 306b), and is not fixed to the stent-containing tubular member 305.

In addition, in the stent delivery system 310 according to the present embodiment, the outside diameter of the proximal-side tube 314 is smaller than the outside diameter of a maximum diameter section of the stent delivery system 310 on the distal side relative to the proximal-side tube 314. Therefore, even in the state in which a guide wire extending toward the proximal side from the opening 323 is set along a side surface of the proximal-side tube 314, the outside diameter of the proximal-side tube 314 with the guide wire can be made to be comparable to the outside diameter of the maximum diameter section of the stent delivery system 310 on the distal side relative to the proximal-side tube 314, so that the system can be inserted into a small-diameter blood vessel.

The stent delivery system 310 according to the present embodiment is provided on the proximal side of the proximal-side tube 314 with a pulling wire wind-up mechanism for winding up the pulling wires 306a, 306b so as to move the stent-containing tubular member 305 toward the proximal side.

The stent delivery system 310 according to the present embodiment includes the distal-side tube 312, the stent 1, the proximal-side tube 314, the stent-containing tubular member 305, the pulling wires 306a, 306b, the slide tube 317, the fixing tube 318, and an operating section 330 having the wind-up mechanism for winding up the pulling wires 306a, 306b. In addition, the fixing tube 318 interconnects the distal-side tube 312 and the proximal-side tube 314, and has the opening 323 which communicates with a proximal portion of the distal-side tube 312.

Figure 17:
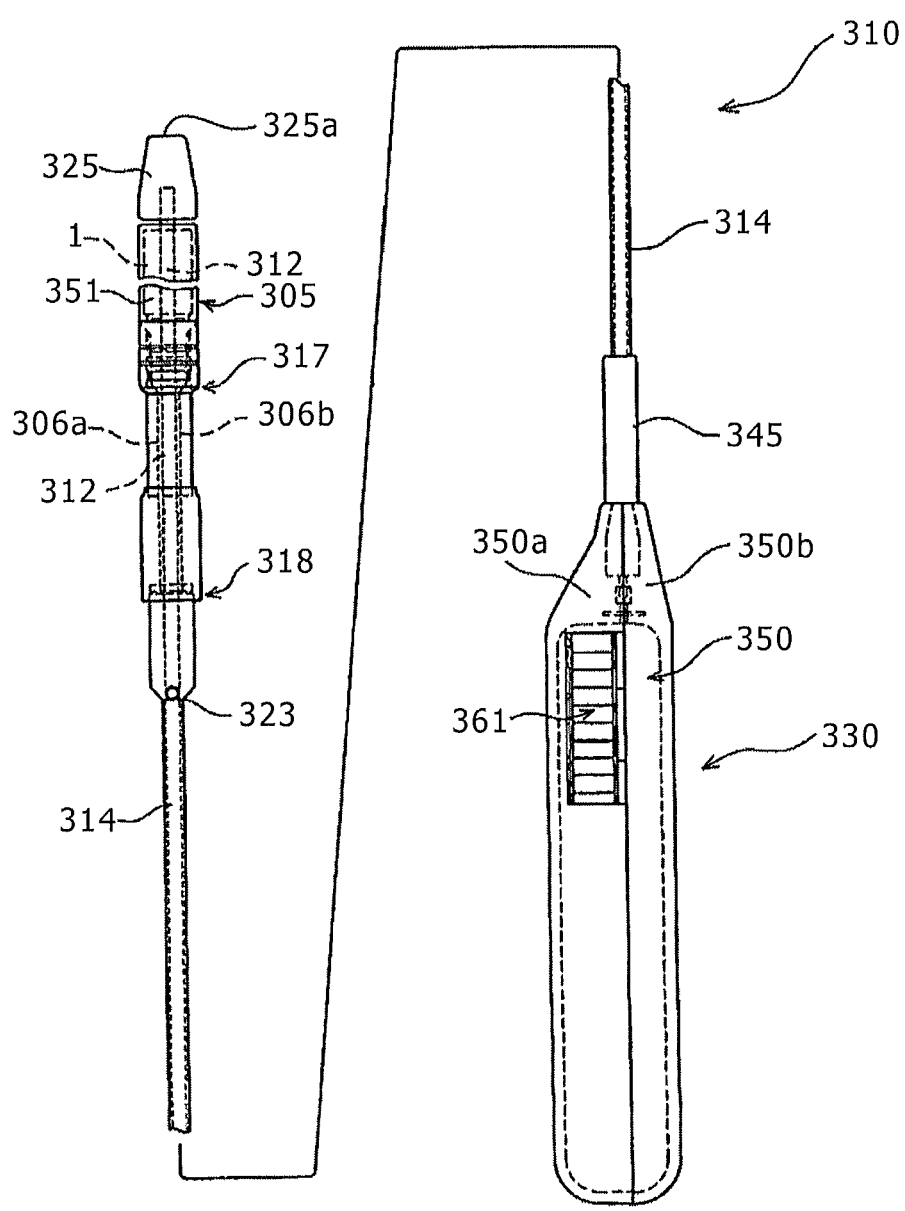
FIG. 17 is an external appearance view of a stent delivery system disclosed here.
Figure 18:
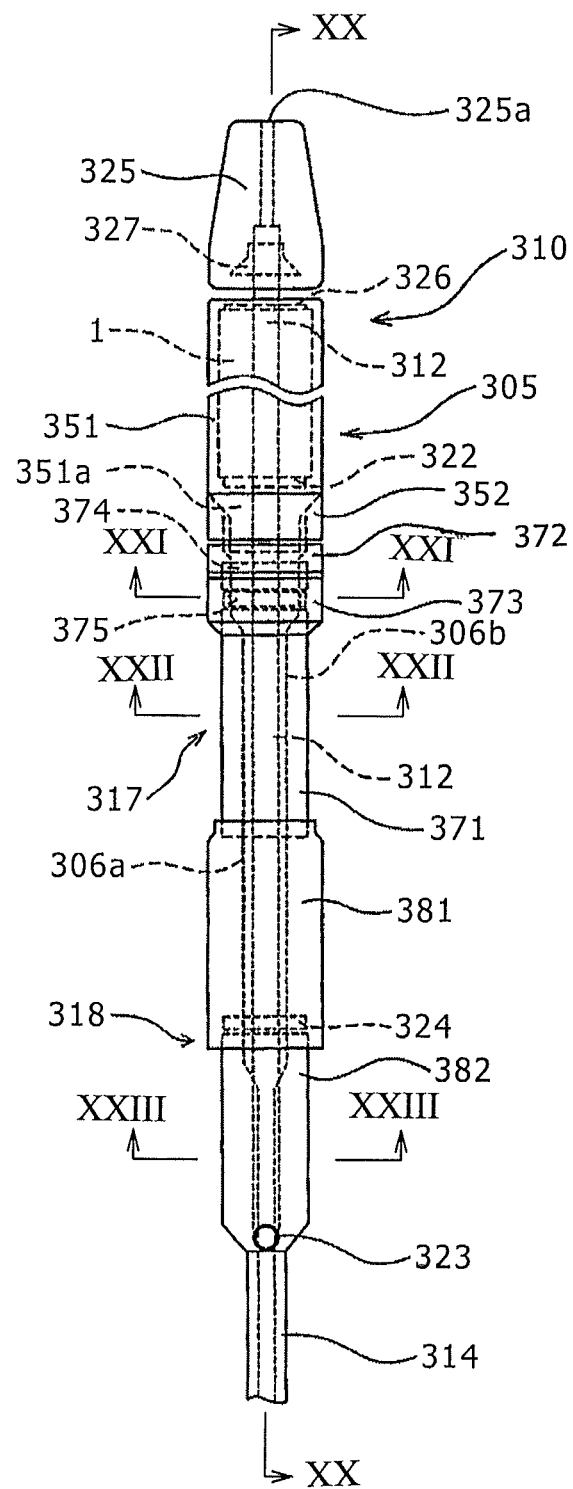
FIG. 18 is an enlarged external appearance view of a distal portion of the stent delivery system of FIG. 17.
Figure 19:
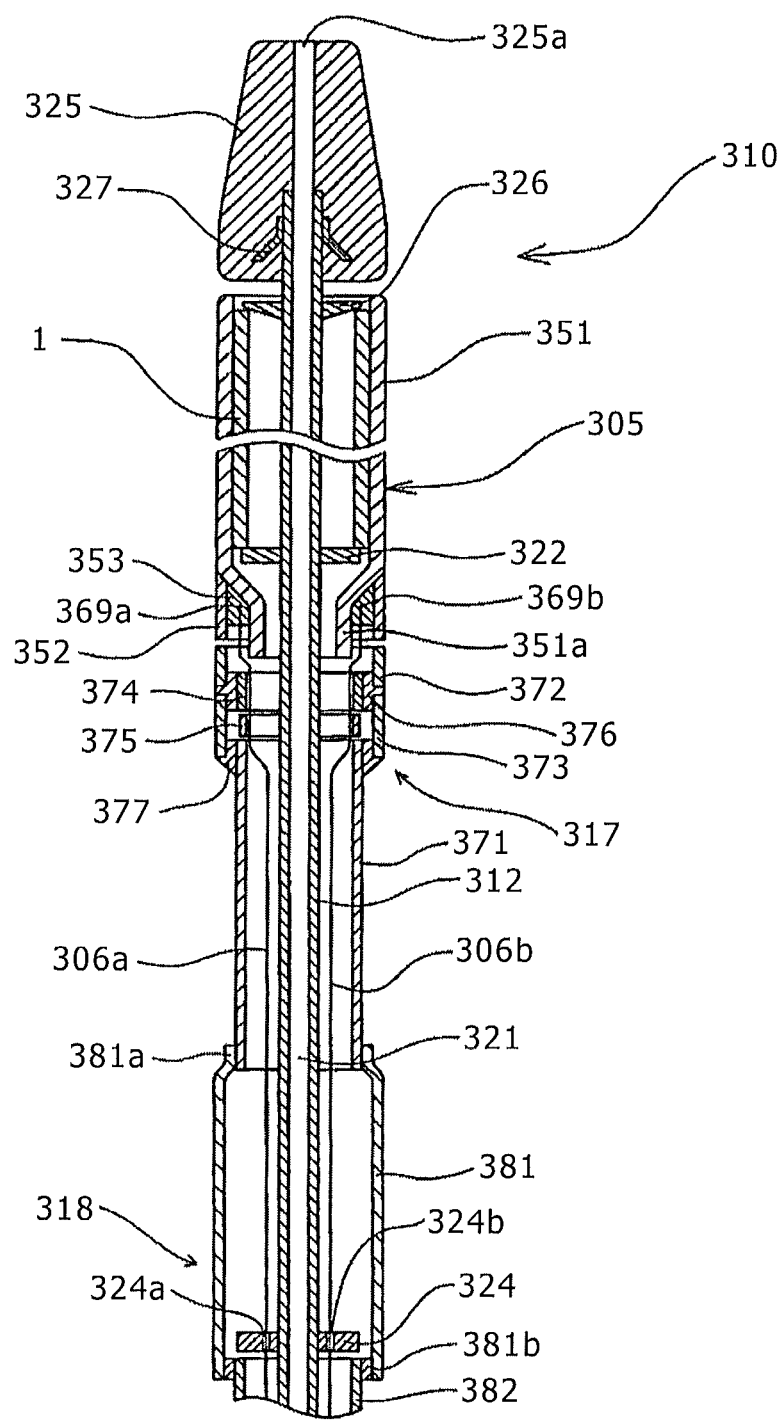
FIG. 19 is an enlarged cross-sectional view of the distal portion of the stent delivery system of FIG. 17.
Figure 20:
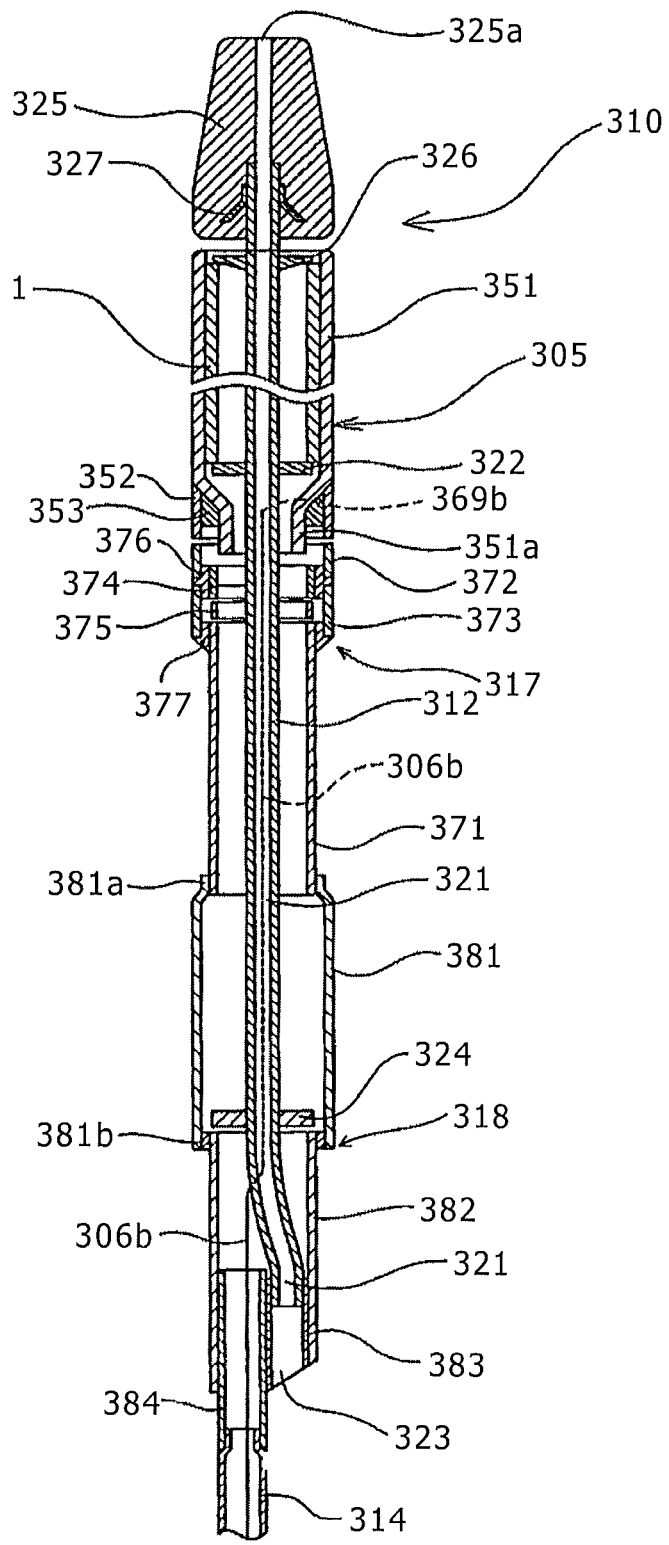
FIG. 20 is a cross-sectional view taken along the section line XX-XX of FIG. 18.
Figure 21:
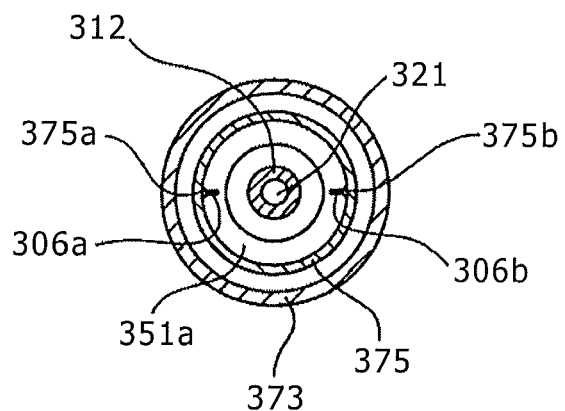
FIG. 21 is an enlarged cross-sectional view taken along the section XXI-XXI of FIG. 18.
Figure 22:
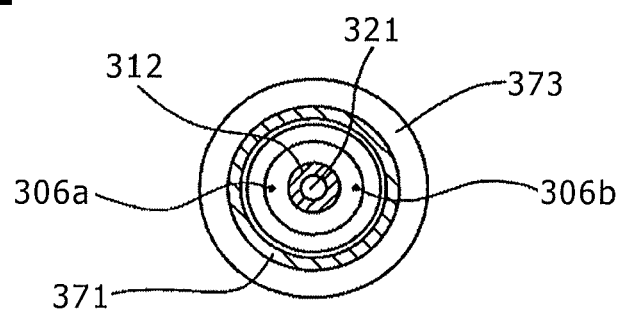
FIG. 22 is an enlarged cross-sectional view taken along the section XXII-XXII of FIG. 18.

As shown in FIGS. 17 to 26, the distal-side tube 312 is a tubular body having a guide wire lumen 321 piercing therethrough from the distal end to the proximal end thereof, its distal portion is composed of a distal end member 325 fixed to its distal end, and the distal end member 325 has a distal opening 325a at the distal end of the distal end member 325. The distal portion may be formed integrally with the distal-side tube 312. In addition, the distal-side tube 312 is fixed to the fixing tube 318 at a proximal portion of the distal-side tube 312. The proximal end of the distal-side tube 312 communicates with the opening 323 formed in the fixing tube 318. As shown in FIG. 20, a proximal portion of the distal-side tube 312 is bent. In addition, as shown in FIGS. 17 and 20, the opening 323 is formed obliquely so as to be slanted toward the proximal side. This facilitates guiding of the guide wire.

The distal-side tube 312 has an outside diameter of 0.3 to 2.0 mm, preferably, 0.5 to 1.5 mm, an inside diameter of 0.2 to 1.5 mm, preferably 0.3 to 1.2 mm, and a length of 20 to 600 mm, preferably 30 to 450 mm.

The distal end member 325 is located on the distal side relative to the distal end of the stent-containing tubular member 305, and, as shown in FIGS. 17 to 20, it is preferably formed in a tapered shape which gradually decreases in diameter toward the distal end. Such a shape facilitates insertion into a stenosed part. In addition, the distal-side tube 312 preferably has a stopper which is provided on the distal side relative to the stent 1 and which inhibits the stent-containing tubular member 305 from moving in the distal direction. In the present embodiment, the proximal end of the distal end member 325 can abut on the distal end of the stent-containing tubular member 305, and functions as the above-mentioned stopper.

The outside diameter of a most distal portion of the distal end member (distal portion) 325 is preferably 0.5 to 1.8 mm. The outside diameter of a maximum diameter section of the distal end member (distal portion) 325 is preferably 0.8 to 4.0 mm. Further, the length of the distal-side tapered section is preferably 2.0 to 20.0 mm.

In addition, as shown in FIGS. 19 and 20, the distal-side tube 312 has the stent proximal end lock section 322 which is provided at a position spaced proximally by a predetermined distance from the distal end of the distal-side tube 312, for the purpose of restricting movement of the stent 1 toward the proximal side. The lock section 322 is preferably an annular projected section. The distal side relative to the section 322 constitutes a stent-containing part. The outside diameter of the lock section 322 is so sized that the lock section 322 can abut on the proximal end of the stent 1 in a compressed state. This helps ensure that even when the stent-containing tubular member 305 is moved toward the proximal side, the lock section 322 maintains the stent 1 in position, resulting in that the stent 1 is released from the stent-containing tubular member 305.

In the stent delivery system 310 according to the present embodiment, as shown in FIGS. 19 and 20, the distal-side tube 312 has a stent distal end lock section 326 provided at a position spaced distally by a predetermined length (approximately the axial length of the stent) from the stent proximal end lock section 322. As shown in FIGS. 19 and 20, the stent distal end lock section 326 is located slightly on the proximal side relative to the distal end of the stent-containing tubular member 305. The lock section 326 is preferably an annular projected section. The part between the stent distal end lock section 326 and the stent proximal end lock section 322 constitutes a stent-containing part. The outside diameter of the lock section 326 is so sized that the lock section 326 can abut on the distal end of the stent 1 in a compressed state. In addition, the lock section 326 has a proximal end surface formed to be a tapered surface which gradually decreases in diameter toward the proximal side. This helps ensure that the stent distal end lock section 326 would not be an obstacle at the time of releasing the stent 1 and that withdrawal of the stent delivery system 310 (specifically, containment thereof into a guiding catheter or a sheath) after the release of the stent 1 is facilitated.

The outside diameters of the stent proximal end lock section 322 and the stent distal end lock section 326 are preferably 0.8 to 4.0 mm. The stent proximal end lock section 322 and the stent distal end lock section 326 are preferably annular projected sections, as shown in the figures; however, they may each be one or a plurality of projections provided integrally with or separately from the distal-side tube 312, insofar as they restrict movement of the stent 1 and permit the stent 1 to be released. In addition, the stent proximal end lock section 322 and the stent distal end lock section 326 may be formed from a radiopaque material as separate members. This enables the position of the stent to be accurately grasped under radioscopy, and facilitates the surgical procedure. Preferable examples of the radiopaque material include gold, platinum, platinum-iridium alloy, silver, stainless steel, and their alloys. In addition, the projections are each attached to the distal-side tube 312 by a method in which a wire formed from a radiopaque material is wound around the outer surface of the distal-side tube 312 or a method in which a pipe formed from a radiopaque material is caulked onto or adhered to the distal-side tube 312.

The material forming the distal-side tube 312 is preferably a material which has hardness and flexibility. Preferable examples of the material include polyolefins such as polyethylene, polypropylene, etc., polyamides, polyesters such as polyethylene terephthalate, etc., fluoro-polymers such as PTFE, ETFE, etc., PEEK (polyether ether ketone), and polyimides. The outer surface of the distal-side tube 312 may be coated with a biocompatible material, particularly an antithrombotic material. Examples of the antithrombotic material which can be suitably used here include polyhydroxyethyl methacrylate, and hydroxyethyl methacrylate-styrene copolymers (e.g., HEMA-St-HEMA block copolymer).

In addition, where the distal portion is composed of a member separate from the distal-side tube 312, the distal portion (distal end member 325) is preferably formed from a flexible material. Examples of the flexible material include synthetic resin elastomers such as olefin elastomers (e.g., polyethylene elastomer, polypropylene elastomer), polyamide elastomers, styrene elastomers (e.g., styrene-butadiene-styrene copolymer, styrene-isoprene-styrene copolymer, styrene-ethylenebutylene-styrene copolymer), urethane elastomers, fluoro-resin elastomers, etc., synthetic rubbers such as urethane rubber, silicone rubber, butadiene rubber, etc., and natural rubbers such as latex rubber, etc.

Particularly, in the stent delivery system 310 according to the present embodiment, the distal-side tube 312 and the distal end member 325 are formed as separate members, and a stopper member 327 is fixed to a distal portion of the distal-side tube 312. The stopper member 327 has a tubular section fixed to the distal-side tube 312, and a skirt section spreading in a tapered form from the tubular section. The stopper member 327 is in the state of being embedded in the distal end member 325, thereby preventing the distal end member 325 from slipping off or moving toward the distal side. The stopper member 327 is preferably formed from a metal (for example, stainless steel).

As shown in FIGS. 17, 18 and 20, the proximal-side tube 314 is a tubular body having a lumen piercing therethrough from the distal end to the proximal end thereof, and has the operating section 330 fixed to the proximal end of the proximal-side tube 314. A distal portion of the proximal-side tube 314 is joined to the fixing tube 318 by a fixing member 384. The lumen of the proximal-side tube 314 permits the pulling wires 306a, 306b to pass through the lumen.

The proximal-side tube 314 has a length of 300 to 1,500 mm, preferably 1,000 to 1,300 mm, an outside diameter of 0.5 to 1.5 mm, preferably 0.6 to 1.3 mm, and an inside diameter of 0.3 to 1.4 mm, preferably 0.5 to 1.2 mm.

The distance of offset between the center axis of the proximal-side tube 314 and the center axis of the distal-side tube 312 is preferably 0.1 to 2.0 mm, more preferably 0.5 to 1.5 mm.

The material forming the proximal-side tube 314 is preferably a material which has hardness and flexibility. Preferable examples of the material include polyolefins such as polyethylene, polypropylene, etc., polyamides, polyesters such as polyethylene terephthalate, etc., fluoro-polymers such as PTFE, ETFE, etc., PEEK (polyether ether ketone), and polyimides. The outer surface of the proximal-side tube may be coated with a biocompatible or antithrombotic material. Examples of the antithrombotic material include polyhydroxyethyl methacrylate, and hydroxyethyl methacrylate-styrene copolymers (e.g., HEMA-St-HEMA block copolymer). In addition, a material comparatively high in rigidity may also be used as the material for forming the proximal-side tube 314. Examples of such comparatively rigid material include metals such as Ni—Ti alloys, brass, stainless steel, aluminum, etc., and resins comparatively high in rigidity, such as polyvinyl chloride, and polycarbonate.

Figure 26:
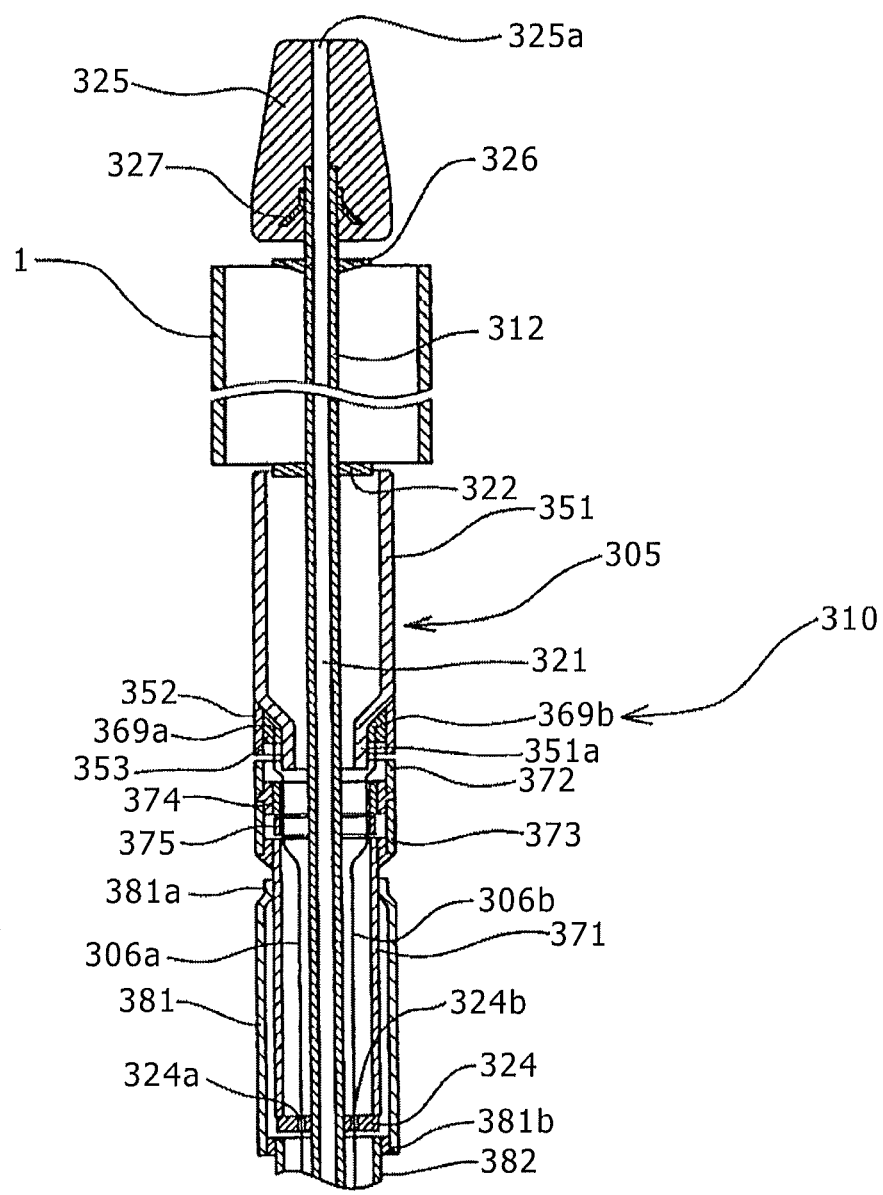
FIG. 26 is an illustration of an operation of the stent delivery system according to one embodiment disclosed here.

As shown in FIGS. 17 to 21 and 24, the stent-containing tubular member 305 is a tubular body having a predetermined length, and is opened at its distal end and at its proximal end. The distal opening functions as a release port for the stent 1 at the time of setting the stent 1 indwelling in a stenosed part of a blood vessel. As shown in FIG. 26, by being pushed out via the distal opening, the stent 1 is relieved from a stress load and expands radially outwardly to be restored to its pre-compression shape.

The length of the stent-containing tubular member 305 is preferably 20 to 400 mm, more preferably 30 to 300 mm. In addition, the outside diameter of the stent-containing tubular member 305 is preferably 1.0 to 4.0 mm, and more preferably 1.5 to 3.0 mm. The inside diameter of the stent-containing tubular member 305 is preferably 1.0 to 2.5 mm.

In addition, the stent-containing tubular member 305 includes a tubular member body section 351 having a reduced diameter section 351a provided at a proximal portion of the tubular member body section 351, and a tubular section 352 provided so as to enclose the reduced diameter section 351a. A proximal portion of the reduced diameter section 351a protrudes beyond the tubular section 352. Distal portions 369 (369a, 369b) of the pulling wires 306 (306a, 306b) enter into a gap formed between the reduced diameter section 351a and the tubular section 352, and are fixed to the stent-containing tubular member 305 by a fixing agent 353 filling the gap. The reduced diameter section 351a has a tapered portion decreasing in outside diameter toward the proximal side, and a short cylindrical portion extending toward the proximal side from the tapered portion. In addition, the tubular section 352 is fixed to a proximal portion of the tubular member body section 351 so as to enclose the reduced diameter section 351a of the tubular member body section 351. Therefore, the reduced diameter section 351a of the tubular member body section 351 constitutes an annular projected section projecting into the inside of the tubular member 305 and toward the proximal side. An annular cavity section is formed between the annular projected section and the inner surface of the stent-containing tubular member 305 (specifically, an inner surface of the tubular section 352). In addition, in the present embodiment, the distal portions 369a, 369b of the pulling wires 306a, 306b are fixed at the outer surface of the reduced diameter section 351a. The cavity section is filled with the fixing agent (adhesive) 353, whereby the tubular member body section 351 and the tubular section 352 are united. In addition, the distal portions (fixation points) 369 (369a, 369b) of the pulling wires 306 (306a, 306b) are fixed to the tubular member 305 by the fixing agent or the like filling the annular cavity section. As the fixing agent, there is preferably used an adhesive such as an epoxy resin, a UV-curing resin, a cyanoacrylate resin, etc., but the fixation may be made by thermal welding (fusing).

In the stent-containing tubular member 305 used in the present embodiment, the tubular member body section 351 and the tubular section 352 are approximately equal in outside diameter. The outside diameter of a stent-containing part of the stent-containing tubular member 305 is preferably 1.0 to 4.0 mm, more preferably 1.5 to 3.0 mm. The length of the stent-containing tubular member 305 is preferably 20 to 400 mm, more preferably 30 to 300 mm. The length of the tubular member body section 351 is preferably 10 to 200 mm, more preferably 15 to 150 mm. The length of the tubular section 352 is preferably 10 to 200 mm, more preferably 15 to 150 mm.

The stent-containing tubular member 305 is not restricted to the one having the tubular member body section 351 and the tubular section 352 as above-mentioned, and it may be an integral one.

The slide tube 317 is so disposed that its distal end is proximate to the proximal end of the stent-containing tubular member 305. In addition, the slide tube 317 can be contained in the fixing tube 318. Alternatively, the slide tube 317 may be fitted over the fixing tube 318. The slide tube 317 is capable of being moved toward the proximal side together with the stent-containing tubular member 305 by pulling of the pulling wires 306 (306a, 306b), and is not fixed to the stent-containing tubular member 305.

In addition, in the stent delivery system 310 according to the present embodiment, there is provided a ring-shaped member 375 which is contained in the slide tube 317 in a non-fixed state and is moved together with the slide tube 317. The pulling wires 306a, 306b are fixed to the inner surface of the ring-shaped member 375. The slide tube 317 has a ring-shaped member retaining section which permits turning of the ring-shaped member 375 but substantially inhibits axial movement of the ring-shaped member 375. The turnable nature of the ring-shaped member 375 relative to the slide tube 317 helps ensure that the ring-shaped member 375, the fixing portions for the pulling wires and the pulling wires themselves would not easily follow up to the turning of the slide tube 317.

Figure 24:
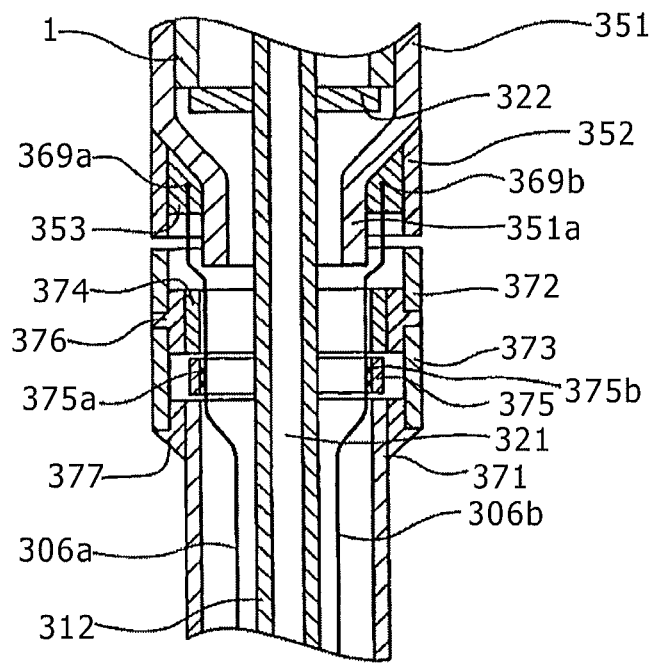
FIG. 24 is an enlarged cross-sectional view in the vicinity of a proximal portion of a stent-containing tubular member and a distal portion of a slide tube in the stent delivery system of FIG. 17.

Specifically, as shown in FIGS. 18 to 22 and 24, the slide tube 317 includes a slide tube body 371, and a distal-side member fixed to the distal end of the slide tube body 371 and being greater than the slide tube body 371 in outside diameter and inside diameter. In the present embodiment, as shown in FIG. 24, the distal-side member of the slide tube 317 includes: an outside tube section having a first tubular member 372 and a second tubular member 373 approximately equal to the first tubular member 372 in outside diameter and inside diameter; an inside tube section having a third tubular member 374 which is disposed inside a proximal portion of the first tubular member 372 and a distal portion of the second tubular member 373; and an anchoring section 376 for fixing the outside tube section and the inner tube section, specifically, for anchoring (firmly attaching) the first tubular member 372 and the second tubular member 373 and the third tubular member 374 to one another. In addition, a proximal portion of the second tubular member 373 (which is the outside tube section) is fixed to a distal portion of the slide tube body 371 by an anchoring section 377. A distal portion of the slide tube body 371 enters into a proximal portion of the second tubular member 373 (which is the outside tube section), and is spaced by a predetermined distance from a proximal portion of the third tubular member 374 which constitutes the inside tube section. As a result, an annular cavity constituting a ring-shaped member retaining section is defined by the distal portion of the slide tube body 371, the inner surface of the second tubular member 373 (which is the outside tube section), and the proximal portion of the third tubular member 374 constituting the inside tube section. In addition, the ring-shaped member 375 is contained in the annular cavity formed as the ring-shaped member retaining section. The ring-shaped member 375 is fixed to none of the slide tube body 371, the second tubular member 373 and the third tubular member 374, so that it is turnable. However, its axial movement within the slide tube 317 is impossible, except for movement corresponding to the clearance. As the ring-shaped member 375, a metallic ring is preferably used. As shown in FIG. 24, the pulling wires 306a, 306b are fixed to the inner surface of the ring-shaped member 375 by fixation points 375a and 375b. Welding, an adhesive or the like is used for the fixation. Fixing the pulling wires 306a and 306b to the ring-shaped member 375 helps ensure that by pulling of the pulling wires 306a and 306b, the ring-shaped member 375 is also pulled, and the slide tube body 371 is, by being pushed from the distal side by the ring-shaped member 375, also moved toward the proximal end of the stent delivery system 310.

The slide tube 317 preferably has its distal portion enclosing a proximal portion of the reduced diameter section 351a of the stent-containing tubular member 305. In addition, the slide tube 317 and the stent-containing tubular member 305 are preferably not bonded to each other. In the present embodiment, as shown in FIGS. 20 and 24, the distal portion of the slide tube 317 encloses the proximal portion of the reduced diameter section 351a of the stent-containing tubular member 305 without being bonded to the latter and, further, substantially without making contact with the latter. Specifically, a distal portion of the first tubular member 372 constituting the outside tube section encloses the proximal portion of the reduced diameter section 351a of the stent-containing tubular member 305, substantially without making contact with the latter.

In the stent delivery system 310 according to the present embodiment, as shown in FIGS. 18 to 20, 23 and 25, the fixing tube 318 includes a distal-side fixing tube 381 having a large outside diameter, and a proximal-side fixing tube 382 fixed to a proximal portion of the distal-side fixing tube 381. In addition, the distal-side fixing tube 381 has a distal reduced diameter section 381a, of which an inner surface is in contact with an outer surface of a proximal portion of the slide tube 317. The slide tube 317 is not fixed to the distal-side fixing tube 381, and, by sliding toward the proximal side, the slide tube 317 enters into and is contained in the distal-side fixing tube 381.

As in the present embodiment, the slide tube 317 is preferably of the type of being contained into the fixing tube 318 through sliding, but this is not restrictive; another type may be adopted in which, with the slide tube slid toward the proximal side, the slide tube is fitted over the fixing tube.

Figure 25:
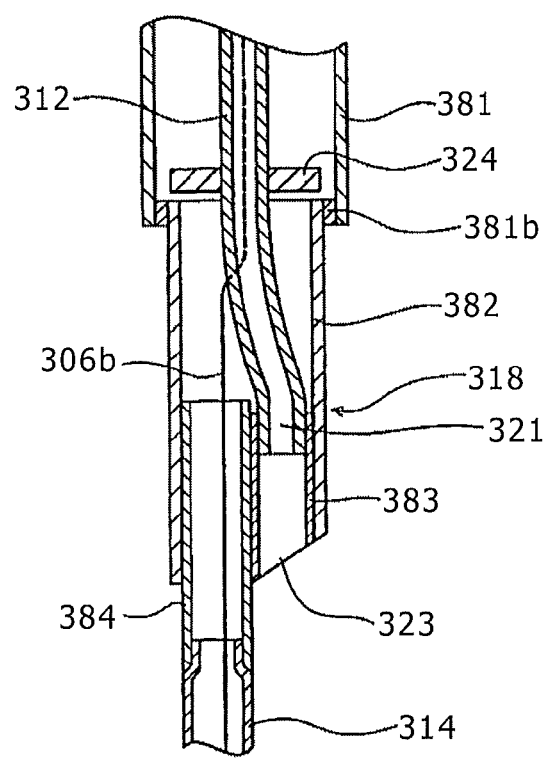
FIG. 25 is an enlarged cross-sectional view in the vicinity of a proximal-side portion of a fixing tube in the stent delivery system of FIG. 17.

A distal portion of the proximal-side fixing tube 382 enters into the proximal end of the distal-side fixing tube 381, and is fixed by a fixing section 381b. In addition, the distal-side tube 312 is provided on its outer surface with a slide tube lock section 324 located in the fixing tube 318, specifically, at a position corresponding to a proximal portion of the distal-side fixing tube 381, as shown in FIG. 25. The slide tube 317 can be slid toward the proximal side until it abuts on the slide tube lock section 324. In other words, by abutment on the slide tube lock section 324, the slide tube 317 is restricted from moving further toward the proximal side.

Figure 23:
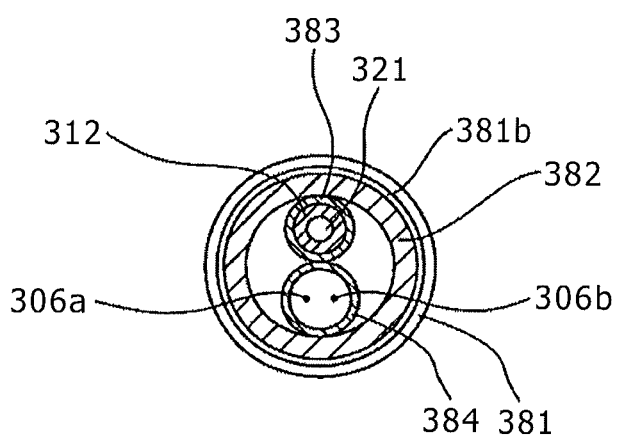
FIG. 23 is an enlarged cross-sectional view taken along the section XXIII-XXIII of FIG. 18.

Further, in the present embodiment, at a proximal portion of the distal-side tube 312, a tubular anchoring member 383 containing the distal-side tube 312 is provided. In addition, a tubular fixing member 384 is provided at the distal end of the proximal-side tube 314. As shown in FIGS. 23 and 25, the tubular anchoring member 383 and the tubular fixing member 384 are firmly attached to the proximal-side fixing tube 382.

As described above and shown in FIGS. 18 and 19, this embodiment of the stent delivery system 310 disclosed by way of example includes a plurality (specifically, two) of pulling wires 306a, 306b. The pulling wires 306a, 306b have their portions at fixation points 369a, 369b fixed to the outside of the reduced diameter section 351a of the stent-containing tubular member 305 by a fixing agent 353, in the cavity section possessed by the tubular member 305 described above. The pulling wires 306a, 306b are, and the fixation points 369a and 369b are, spaced apart by a predetermined length.

Examples of the materials for forming the stent-containing tubular member 305 (the tubular member body section 351, the tubular section 352), the slide tube 317 (the slide tube body 371) and the fixing tube 318 (the distal-side fixing tube 381, the proximal-side fixing tube 382) include polyolefins such as polyethylene, polypropylene, etc., polyamides, polyesters such as polyethylene terephthalate, etc., polyimides, fluro-polymers such as PTFE, ETFE, etc., and thermoplastic elastomers. The thermoplastic elastomers are appropriately selected from among nylon-based ones (e.g., polyamide elastomers), urethane-based ones (e.g., polyurethane elastomers), polyester-based ones (e.g., polyethylene terephthalate elastomer), and olefin-based ones (e.g., polyethylene elastomer, polypropylene elastomer).

Further, an outer surface of the stent-containing tubular member 305 is preferably subjected to a treatment for making the outer surface exhibit lubricating properties. Examples of such a treatment include a method in which a hydrophilic polymer such as polyhydroxyethyl methacrylate, polyhydroxyethyl acrylate, hydroxypropyl cellulose, methyl vinyl ether-maleic anhydride copolymer, polyethylene glycol, polyacrylamide, polyvinylpyrrolidone, dimethylacrylamide-glycidyl methacrylate copolymer, etc. is applied to or fixed to the outer surface of the stent-containing tubular member 305. In addition, the above-mentioned hydrophilic polymer may be applied to or fixed to an inner surface of the stent-containing tubular member 305, for promising better sliding of the stent 1.

The stent-containing tubular member 305 may be formed by use of a combined two-layer structure of the above-mentioned polymers (e.g., an outer surface formed of polyamide and an inner surface formed of PTFE).

In addition, the stent delivery system 310 has the pulling wires 306 (306a, 306b) each of which has one end section fixed to a proximal portion of the stent-containing tubular member 305, extends beyond the proximal end of the stent-containing tubular member 305, penetrates the slide tube 317 and the fixing tube 318, and extends inside the proximal-side tube 314. With the pulling wires 306 (306a, 306b) pulled toward the proximal side of the proximal-side tube, the stent-containing tubular member 305 and the slide tube 317 are moved toward the proximal side.

In addition, as shown in FIGS. 17, 18, 21 to 24 and 26, this embodiment of the stent delivery system 310 disclosed by way of example includes a plurality (specifically, two) of pulling wires 306a and 306b, and the pulling wires 306a and 306b are fixed to a proximal portion of the stent-containing tubular member 305 by the fixation points 369a and 369b. The fixation points 369a and 369b are so disposed as to be spaced from each other by a predetermined distance.

Further, in the present embodiment, the pulling wires 306a and 306b are fixed also to a member or members to be moved by pulling. Specifically, as shown in FIG. 24 and above-mentioned, the pulling wires 306a and 306b are fixed also to the ring-shaped member 375 (specifically, its inner surface) possessed by the slide tube 317. In the stent delivery system 310 according to the present embodiment, therefore, with the pulling wires 306a and 306b pulled toward the proximal side, the ring-shaped member 375 is also pulled toward the proximal side, and, due to the abutment of the slide tube 317 (the slide tube body 371) to the ring-shaped member 375, the slide tube 317 is also pulled toward the proximal side. In the present embodiment, accordingly, the stent-containing tubular member 305 and the slide tube 317 are pulled independently of each other, and the stent-containing tubular member 305 and the slide tube 317 do not make contact with each other at the time of pulling. In addition, the forces at the time of pulling of the pulling wires 306a and 306b are dispersed to the fixation points 369a and 369b and to the fixation points 375a and 375b of the ring-shaped member 375 which is a member moved by the pulling, so that the fixation between the pulling wires 306a; 306b and the stent-containing tubular member 305 at the fixation points 369a, 369b is securely prevented from being released.

In the stent delivery system 310 according to the present embodiment, as shown in FIG. 17, the pulling wires 306 penetrate the proximal-side tube 314, and extend beyond the proximal end of the proximal-side tube 314.

The pulling wires 306 can be composed of a wire or strand of a plurality of wires. In addition, the diameter of the pulling wires 306 is not particularly limited; normally, it is preferably 0.01 to 0.55 mm, more preferably 0.1 to 0.3 mm.

Examples of the material for forming the pulling wires 306a and 306b include stainless steel wires (preferably, high tensile stainless steel for spring), piano wires (preferably, nickel-plated or chromium-plated piano wire), and superelastic alloy wires; wires of various metals such as Ni—Ti alloy, Cu—Zn alloy, Ni—Al alloy, tungsten, tungsten alloys, titanium, titanium alloys, cobalt alloys, tantalum, etc.; polymer materials having comparatively high rigidity such as polyamides, polyimides, ultra-high-molecular-weight polyethylene, polypropylene, fluoro-resins, etc.; and appropriate combinations thereof.

In addition, side surfaces of the pulling wires 306a and 306b may be coated with a low-friction resin for increasing lubricity. Examples of the low-friction resin include fluoro-resins, 6,6-nylon, polyether ether ketone, and high-density polyethylene. Among them, preferred are fluoro-resins. Examples of the fluoro-resins include polytetrafluoroethylene, polyvinylidene fluoride, ethylene-tetrafluoroethylene, and perfluoroalkoxy resins. Coatings of silicone and various hydrophilic resins may also be adopted.

As shown in FIG. 19, the pulling wires 306a and 306b are not fixed to the slide tube lock section 324 but pass through passages 324a and 324b formed in the slide tube lock section 324.

The stent 1 is contained in the stent-containing tubular member 305. The stent 1 positioned in the stent-containing tubular member 305 can be the self-expandable stent according to any of the above-described embodiments.

As shown in FIGS. 17 and 27 to 31, the stent delivery system 310 according to the present embodiment has the operating section 330 fixed to the proximal end of the proximal-side tube 314.

The operating section 330 of the stent delivery system 310 according to the present embodiment includes, in addition to the pulling wire wind-up mechanism, a locking mechanism for unlockably locking the rotation of the pulling wire wind-up mechanism, and a reverse rotation restricting mechanism for restricting rotation in the direction reverse to a pulling wire wind-up direction of the pulling wire wind-up function.

As shown in FIGS. 27 to 31, the operating section 330 has an operating section housing 350. The operating section housing 350 includes a first housing 350a and a second housing 350b. The operating section housing 350 has a shape which is bent and rounded on the proximal side and at a central portion thereof so that the operating section housing 350 is relatively easy to grip and that a roller 361 can be operated rather easily when the operating section housing 350 is in a gripped state.

Figure 29:
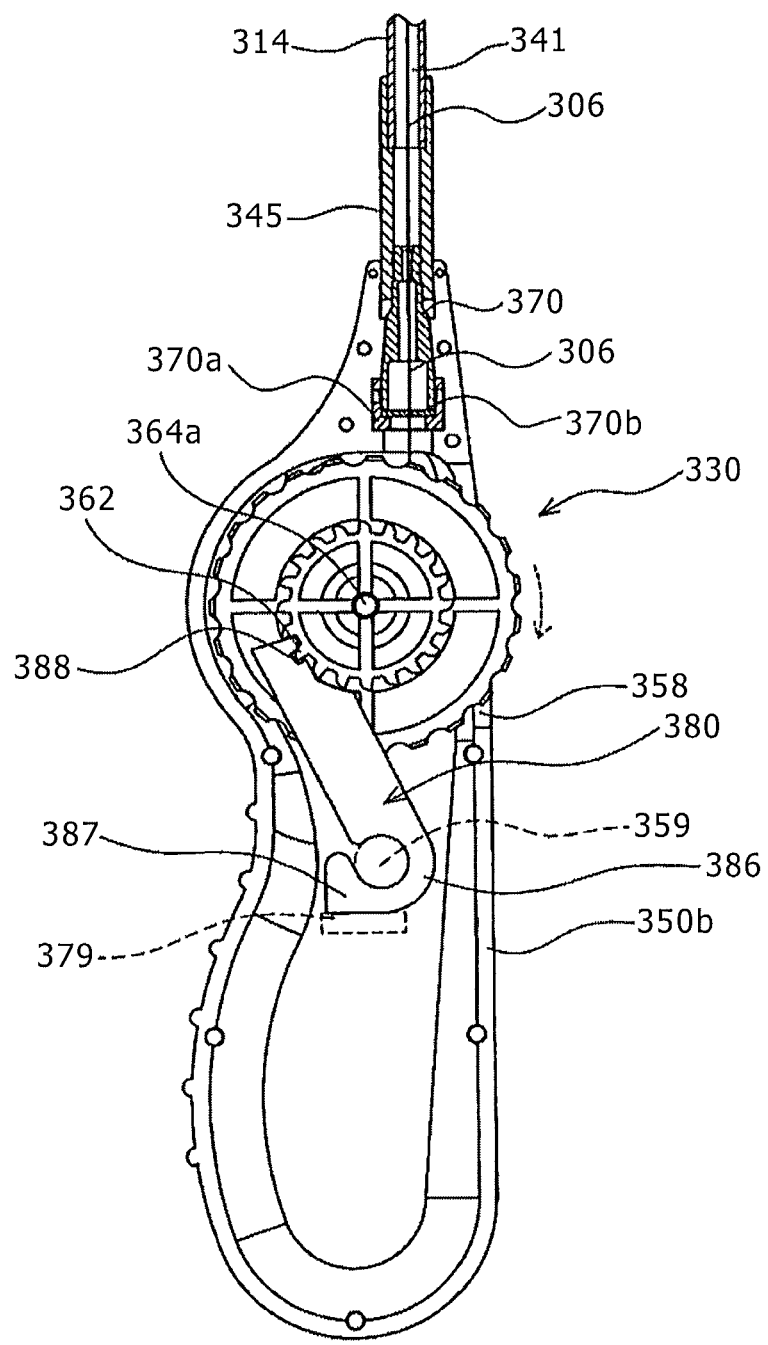
FIG. 29 is an illustration of an internal structure of the operating section of the stent delivery system shown in FIG. 27.

In addition, as shown in FIG. 29, a distal portion of a tubular connector 345 is fixed to the proximal end of the proximal-side tube 314. A lumen in the tubular connector 345 communicates with a lumen 341 in the proximal-side tube 314. A seal mechanism connected to a proximal portion of the connector 345 is contained in the operating section housing 350. As shown in FIG. 29, the seal mechanism includes a seal mechanism tubular body member 370 having a distal portion fixed to a proximal portion of the connector 345, a cap member 370a fixed to the proximal end of the tubular body member 370, and a seal member 370b disposed between the tubular body member 370 and the cap member 370a. The tubular body member 370 and the cap member 370a are each provided with an opening section piercing therethrough. The seal member 370b is provided with hole sections or slits which permit the pulling wires 306 (306a, 306b) to pass therethrough in a liquid-tight condition and slidably.

Figure 27:
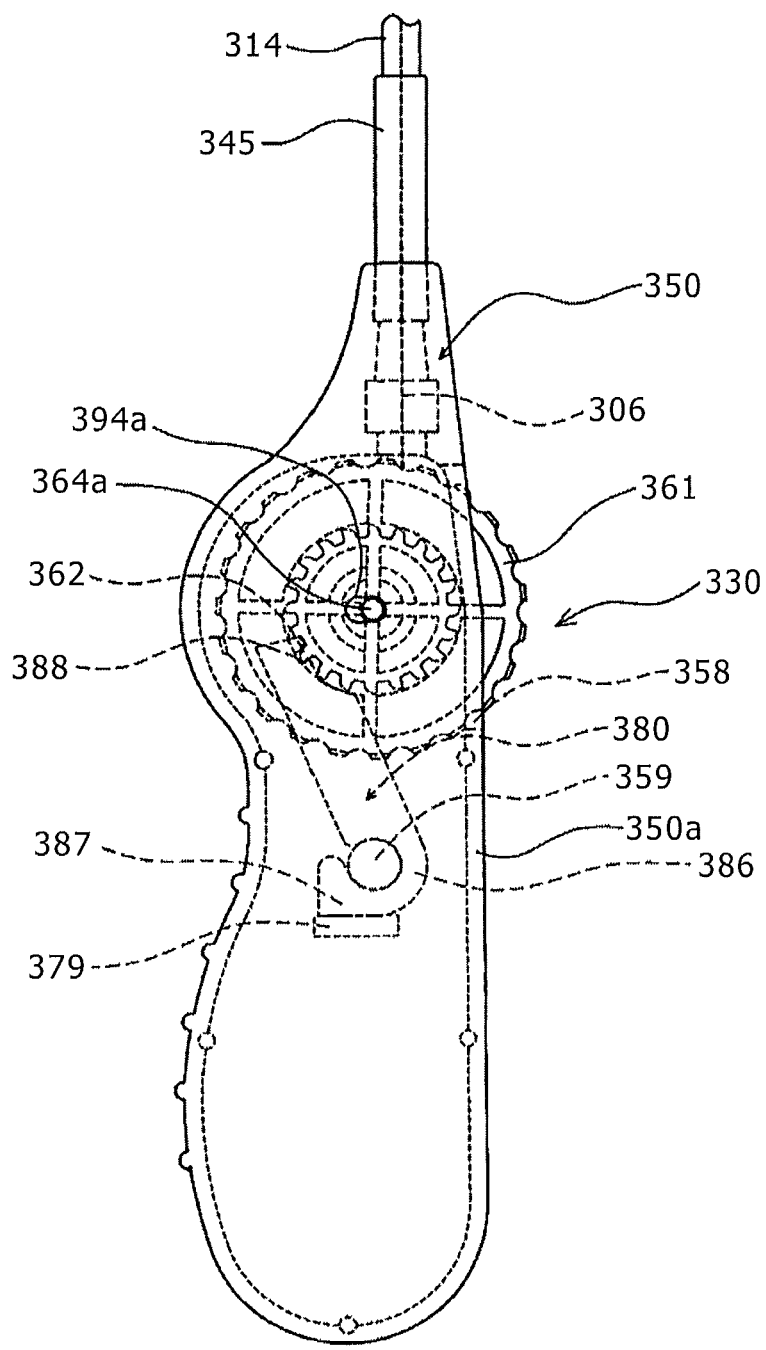
FIG. 27 is an enlarged front view in the vicinity of an operating section of the stent delivery system disclosed here.
Figure 28:
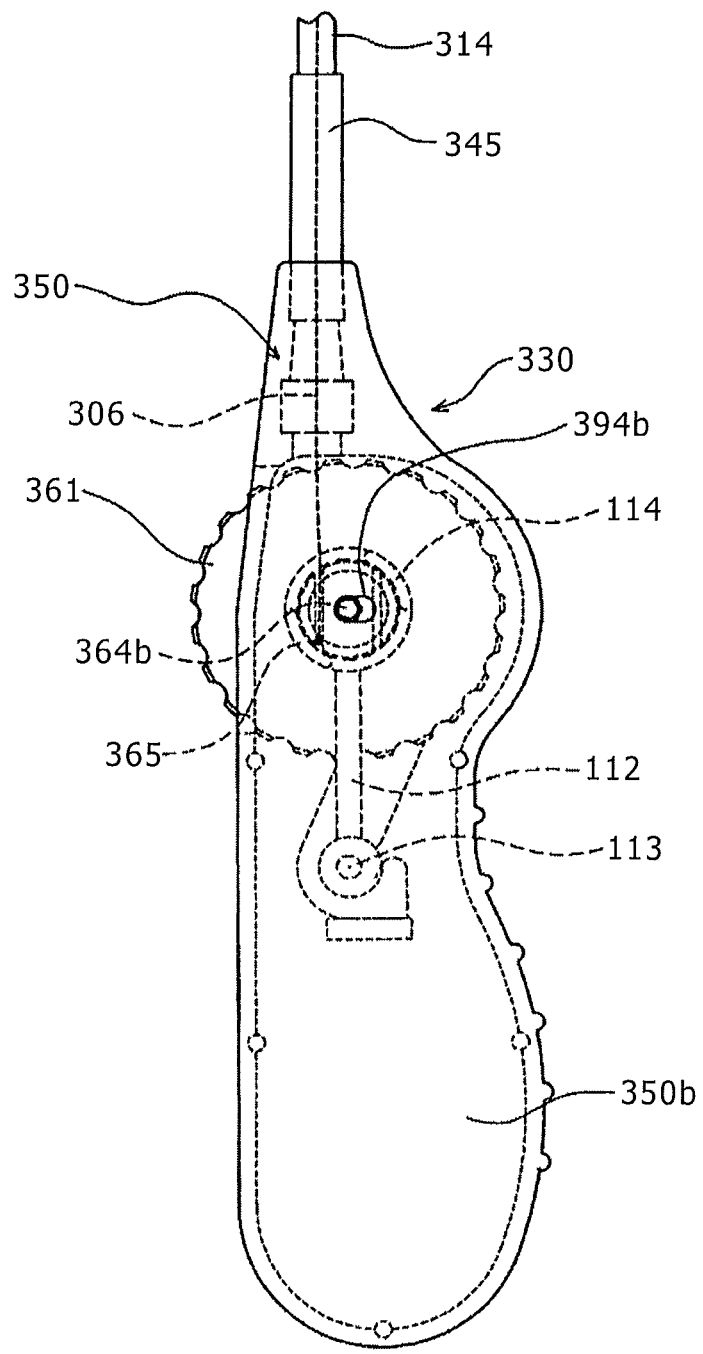
FIG. 28 is an enlarged back view in the vicinity of the operating section of the stent delivery system shown in FIG. 27.

As shown in FIGS. 27 to 30, the housing 350 includes an opening section 358 through which an operational rotating roller 361 partly projects, a locking rib (not shown) to be engaged with projected portions of a gear section 362 provided on the roller 361, a bearing section 394b for containing one end 364b of a rotating shaft of the roller 361, and a bearing section 394a for containing the other end 364a of the rotating shaft of the roller 361. The locking rib is so shaped as to be able to enter between the projected portions formed on the gear section 362 of the roller 361. In addition, as shown in FIGS. 27 and 28, the bearing sections 394a and 394b are formed in a gourd shape such that they contain the one end 364b and the other end 364a of the rotating shaft of the roller 361 and they extend in the direction of spacing away from the above-mentioned opening section. The bearing sections 394a and 394b are not restricted to the gourd shapes, insofar as they allow movement over such a distance that engagement with the locking rib can be released. For example, the bearing sections 394a and 394b may be oblong, rectangular, elliptic or the like in shape. Especially, in the operating section 330 according to the present embodiment, as shown in FIGS. 27 and 28, the bearing sections 394a and 394b are gourd shapes. Therefore, when the operational rotating roller 361 is pressed so that the ends 364a and 364b of the rotating shaft of the roller 361 which are contained in one-end-side spaces of the bearing sections 394a and 394b are caused to ride over mutually facing rib portions formed at inside surfaces in central parts of the bearing sections 394a and 394b, the ends 364a and 364b of the rotating shaft of the roller 361 are put into the state of being contained in the other-end-side spaces of the bearing sections 394a and 394b. The condition shown in FIG. 29 is the condition where the roller 361 is pressed. In this condition, the roller 361 is pressed by a biasing member. However, since the ends 364a, 364b of the rotating shaft of the roller 361 make contact with the mutually facing rib portions formed at the inside surfaces in the central parts of the bearing sections 394a, 394b, the ends 364a, 364b are not moved into the one-end-side spaces of the bearing sections 394a, 394b. Accordingly, the roller 361 is kept in a rotatable state.

Figure 31:
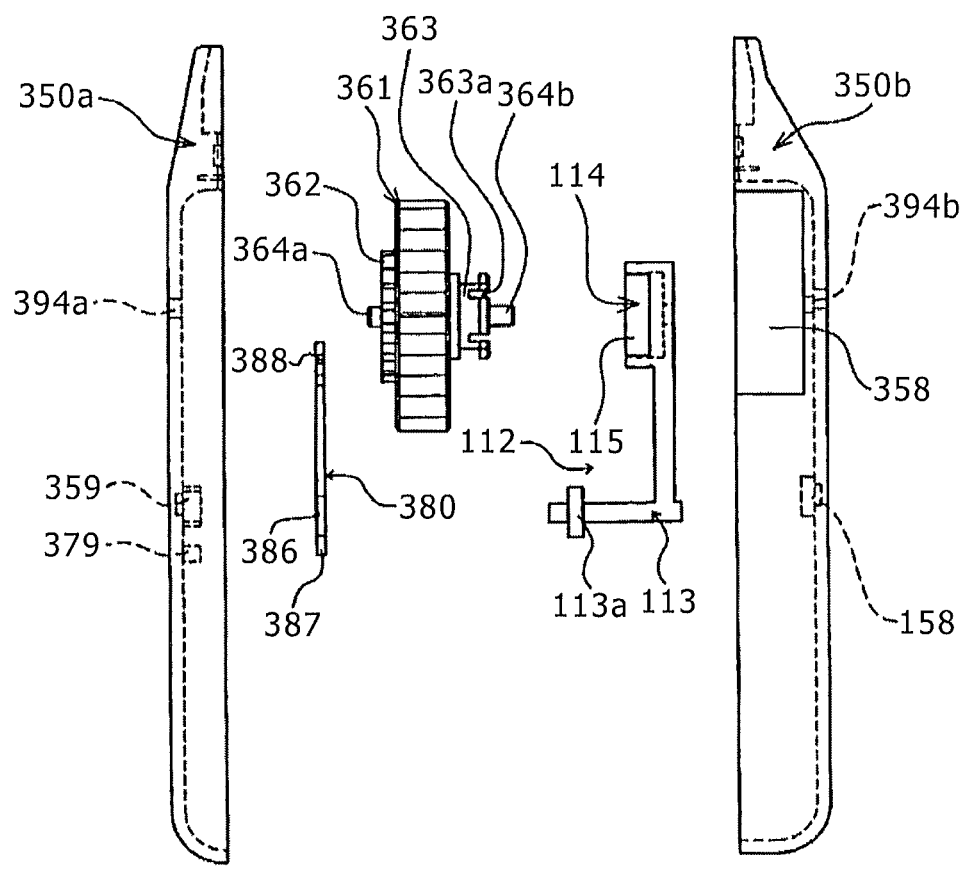
FIG. 31 is an illustration of an internal structure of the operating section of the stent delivery system shown in FIG. 27.

In addition, in the present embodiment, the operating section 330 has a collar member 112, as shown in FIGS. 28 and 31. The collar member 112 has a collar section 114 which contains a wind-up shaft section 363 and which defines an annular space between itself and the wind-up shaft section 363. The collar section 114 prevents the pulling wires wound up on the wind-up shaft section 363 from slackening. In addition, the collar member 112 has a function of guiding a movement upon pressing of the rotating roller and a function of restraining the rotating roller from chattering. A pin 113 of the collar member 112 is rotatably borne by a projected part (bearing part) 359 of the first housing 350a and a recessed part (bearing part) 158 of the second housing 350b. As shown in FIGS. 27 and 31, the bearing sections 394a, 394b are formed in a gently curved circular arc shape, with the pin 113 (the bearing parts 359, 158) as the center of the circle, and the roller 361 is formed so as to have a length permitting the roller 361 to be moved over a distance greater than the height of the locking rib. In addition, as shown in FIG. 31, the collar member 112 has two mutually facing cutouts 115 ranging from side surfaces to a space inside the collar section 114. The pulling wires 306 are each passed through one of the cutouts 115 and fixed to the wind-up shaft section 363.

The pulling wire wind-up mechanism is composed of the roller 361 and the wind-up shaft section 363 rotated by rotation of the roller 361. The wind-up shaft section 363 grips or fixes proximal portions of the pulling wires 306 (306a and 306b). Specifically, as shown in FIG. 28, an anchor part 365 formed to be greater than the pulling wire 306 is provided at a proximal portion of the pulling wire 306, and the wind-up shaft section 363 is provided with a slit 363a in which the pulling wire 306 can be contained. In addition, the proximal portion of the pulling wire 306 is contained in the slit 363a in the wind-up shaft section 363 so that the anchor part 365 is located on the proximal outer side of the slit 363a. This helps ensure that when the wind-up shaft section 363 is rotated, the wire 306 is wound up onto the outer surface of the wind-up shaft section 363. The grip or fixation of the pulling wire 306 onto the wind-up shaft section 363 is not restricted to the above-described as other arrangement are also possible. For example, the proximal end or a proximal portion of the pulling wire 306 may be directly fixed to the wind-up shaft.

The proximal portions of the pulling wires 306 (306a and 306b) to be wound up are preferably flexible, in order to facilitate the wind-up. The proximal portions of the pulling wires 306 (306a and 306b) can be made flexible by, for example, a method in which the proximal portions are formed from a flexible material, or a method in which the proximal portions are made small in thickness (diametral size).

In addition, in the present embodiment, the wind-up shaft section 363 is formed integrally with the rotating roller 361 so as to be coaxial with the latter. Further, as shown in FIG. 31, the wind-up shaft section 363 is provided on an one side surface of the rotating roller 361. With the rotating roller 361 rotated, the wind-up shaft section 363 is also rotated simultaneously. In addition, the amount of the pulling wire 306 wound up is preferably small, as compared with the rotational operating amount of the rotating roller 361. This helps ensure that the pulling wires 306 (306a and 306b) can be wound up slowly, and the movement of the stent-containing tubular member 305 toward the proximal side is made relatively slow and favorable. In the present embodiment, the outside diameter of the wind-up shaft section 363 is smaller than the diameter of the rotating roller 361, so that the amount of the pulling wire 306 wound up is small as compared with the rotational operating amount of the rotating roller 361.

The outside diameter of the wind-up shaft section 363 is preferably 1 to 60 mm, more preferably 3 to 30 mm, and the outside diameter of the rotating roller 361 is preferably 1 to 20 times, more preferably 1 to 10 times, the outside diameter of the wind-up shaft section 363. In addition, the outside diameter of the rotating roller 361 is preferably 10 to 60 mm, more preferably 15 to 50 mm.

The rotating roller and the wind-up shaft section are not restricted to such an integral body, and the wind-up shaft section may be one composed of a separate member which is rotated following up to the rotation of the rotating roller. The transmission system for rotation of the rotating roller may be gear type or belt type or the like. The surface part which may be contacted at the time of operating the roller 361 is preferably made to be a surface which is difficultly slidable. For instance, the surface part which may be contacted at the time of operating the roller 361 is preferably subjected to a knurling treatment, an embossing treatment, coating with a high-friction material, or the like.

In addition, the operating section 330 according to the present embodiment includes the locking mechanism for unlockably locking the rotation of the pulling wire wind-up mechanism, and the reverse rotation restricting mechanism for restricting rotation in the direction reverse to the pulling wire wind-up direction of the pulling wire wind-up function.

As shown in FIGS. 29 and 31, the operational rotating roller 361 has the gear section 362 so provided as to be rotated coaxially and integrally therewith. Further, as shown in FIG. 31, the gear section 362 is provided on an other side surface of the rotating roller 361 (in other words, at a surface on the side opposite to a surface where the wind-up shaft section 363 is provided). Therefore, the gear section 362 and the wind-up shaft section 363 are in the state of being partitioned from each other by a wall composed of the operational rotating roller 361.

The operational rotating roller 361 is partly exposed via the opening section, and the exposed part constitutes an operating part. In addition, the rotating roller 361 has that other end 364a of the rotating shaft which is provided at the other side surface thereof (specifically, a side surface of the gear section) and that one end 364b of the rotating shaft which is provided at the one side surface thereof (specifically, a side surface of the wind-up shaft section).

Further, biasing means (biasing member) 380 is provided in the housing 350 for biasing the rotating roller 361 toward the opening section of the housing 350. Specifically, the roller 361 is biased by the biasing means 380. Furthermore, the housing 350 is provided with a locking rib (not shown) which can enter between the projected parts of the gear section 362 of the rotating roller 361 biased by the biasing member 380. Therefore, in the state of being biased by the biasing member 380, the rotating roller 361 is in the state shown in FIG. 28, wherein the locking rib is engaged with the projected parts of the gear section 362, so that the rotating roller 361 becomes non-rotatable. When the rotating roller 361 is pressed in the direction of spacing away from the locking rib, the one end 364b and the other end 364a of the rotating shaft of the rotating roller 361 are moved within the bearing sections 394a and 394b provided in the housing 350, to thereby become rotatable. Therefore, the operating section 330 according to the present embodiment restricts rotation in the state of not pressing the rotating roller 361, and has the locking mechanism which unlockably locks the rotation of the pulling wire wind-up mechanism.

Furthermore, in the operating section 330 according to the present embodiment, the above-mentioned biasing means 380 and the above-mentioned gear section 362 constitute the reverse rotation restricting mechanism for restricting rotation in the direction reverse to the pulling wire wind-up direction of the pulling wire wind-up mechanism.

As shown in FIGS. 27 to 29, the operating section 330 is provided therein with the reverse rotation restricting mechanism. In the operating section 330, the biasing member 380 constitutes the reverse rotation restricting mechanism, and the biasing member 380 is also a reverse rotation restricting member. The reverse rotation restricting mechanism includes: a engaging section 388 which is provided at a part facing the gear section 362 of the operational rotating roller 361 at a distal portion of the reverse rotation restricting member (being the biasing member, as well) 380 and which can engage with the gear section; an elastically deformable section 386; and a fixing section 387 for fixing to the housing 350. In addition, the first housing 350a has a first projected part (bearing part) 359 and a second projected part 379 which are formed at an inner surface thereof. The first projected part 359 enters into the elastically deformable section 386 of the reverse rotation restricting member (biasing member) 380, and has an outer surface shape corresponding to the inner surface shape of the elastically deformable section 386. Specifically, the inner surface shape of the elastically deformable section 386 is arcuate shape, and the first projected part 359 has a cylindrical shape corresponding to the arcuate shape. The mounting section 387 of the reverse rotation restricting member (biasing member) 380 has a shape which permits fixing thereof between the first projected part 359 and the second projected part 379 which are possessed by the first housing 350a. In addition, the reverse rotation restricting member (biasing member) 380 has its mounting section 387 fixed between the first projected part 359 and the second projected part 379 of the first housing 350a, thereby being fixed in a non-turnable manner, and biases the operational rotating roller 361 toward the opening section 358 by an elastic force of the elastically deformable section 386. The mounting section 387 of the reverse rotation restricting member (biasing member) 380 is restricted with respect to movement toward side surfaces by a disk-shaped projected part 113a provided on the collar member 112.

Figure 30:
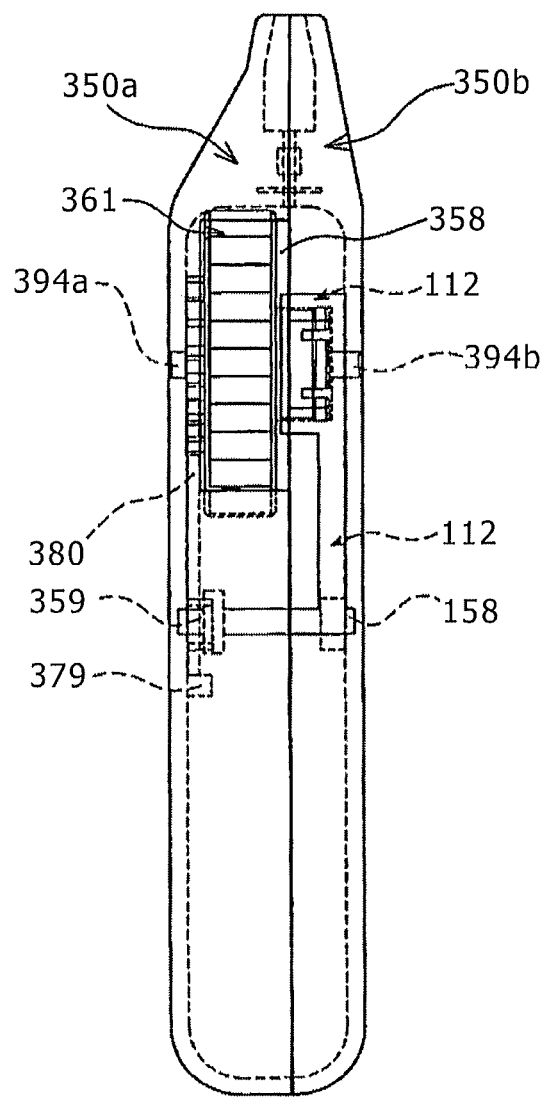
FIG. 30 is a right side view of only the operating section of the stent delivery system shown in FIG. 27.

In addition, as above-mentioned, the roller 361 can be rotated by pressing the roller 361. Though the roller 361 can be rotated in the direction of arrow in FIG. 29 (in the direction for winding up the pulling wires 306a and 306b), however, an attempt to rotate the roller 361 in the reverse direction results in that one tooth part of the gear section 362 is engaged with the engaging section 388 of the reverse rotation restricting member (biasing member) 380, whereby the attempted rotation is inhibited. By this, rotation of the roller 361 in the direction reverse to the pulling wire wind-up direction of the pulling wire wind-up section is restricted. In this operating section 330, as shown in FIG. 30, the reverse rotation restricting member (biasing member) 380 is disposed between an inner surface of the first housing 350a and a side surface of the rotating roller 361. Therefore, movement of the reverse rotation restricting member (biasing member) 380 in lateral directions (horizontal directions) is restricted by the inner surface of the first housing 350a and the side surface of the rotating roller 361.

The gear section 362 is smaller than the rotating roller 361 in diameter. The outside diameter of the gear section 362 is preferably 10 to 60 mm, more preferably 15 to 50 mm. The number of teeth of the gear section 362 is preferably 4 to 200, more preferably 4 to 70.

In addition, the collar member 112 possessed by the operating section 330 has its one end section rotatably borne by the pin 113, whereas the collar section 114 on the other end side contains the wind-up shaft section 363 and defines the annular space between itself and the wind-up shaft section 363. The annular space is not so large a space, and causes a narrower annular space to be formed between outer surfaces of the wires wound up.

Set forth next is a description of an example of a method of using the stent delivery system 310 according to the disclosure here.

First, the proximal end of a guide wire is inserted into the opening 325a of the distal end member of the stent delivery system 310 shown in FIGS. 17 and 18, and the guide wire (not shown) is led out via the opening 323. Next, the stent delivery system 310 is inserted into a guiding catheter (not shown) inserted in a living body, and the stent delivery system 310 is advanced forward along the guide wire so that the stent-containing part of the stent-containing tubular member 305 is positioned in a target stenosed part of a blood vessel or the like.

Subsequently, the operational rotating roller 361 of the operating section 330 is pressed, and thereafter the roller 361 is rotated in the direction of arrow in FIG. 29. By this operation, the pulling wires 306 (306a and 306b) are wound up onto the outer surface of the wind-up shaft section 363, and the stent-containing tubular member 305 and the slide tube 317 are moved along the axial direction toward the proximal side. In this instance, the proximal end surface of the stent 1 abuts on and is locked on the distal end face of the stent proximal end lock section 322 of the distal-side tube 312. As the stent-containing tubular member 305 is moved, therefore, the stent 1 is released via the distal opening of the stent-containing tubular member 305. As a result of this release, as shown in FIG. 26, the stent 1 is permitted to self-expand, thereby dilating the stenosed part and being set indwelling in the stenosed part.

The detailed description above describes features and aspects of embodiments of a stent and a stent delivery system. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent to be brought into contact with tissue in a living body through deformation at the time of indwelling the stent in the living body, the stent comprising:
a plurality of annular bodies arrayed in an axial direction, each of the annular bodies being annularly-shaped from a linear constituent element, each of the annular bodies having a plurality of one-end-side bent sections which are bent sections at one axial end and a plurality of other-end-side bent sections which are bent sections at an opposite axial end;
axially adjacent ones of the annular bodies being linked by link sections; and
the stent including, as said link sections, at least three kinds of link sections selected from four kinds of link sections, the four kinds of link sections including: a vertex-vertex bent link section which links a vertex of one of the other-end-side bent sections of the one-end-side annular body of the axially adjacent bodies with a vertex of one of the one-end-side bent sections of the other-end-side annular body of the axially adjacent annular bodies and which has at least one one-end-side bent part and at least one other-end-side bent part; a central part-central part bent link section which links a central part of a linear portion interconnecting the one-end-side bent section and the other-end-side bent section of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part; a central part-vertex bent link section which links the central part of the linear portion interconnecting the one-end-side bent section and the other-end-side bent section of the one-end-side annular body of the axially adjacent annular bodies with the vertex of one of the one-end-side bent sections of the other-end-side annular body of the axially adjacent annular bodies and which has at least one one-end-side bent part and at least one other-end-side bent part; and a vertex-central part bent link section which links the vertex of one of the other-end-side bent sections of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part, the at least three kinds of the link sections including at least the vertex-vertex bent link section and the central part-central part bent link section, and the axially adjacent annular bodies being linked by at least two different kinds of the four link sections.

2. The stent according to claim 1, wherein all the axially adjacent annular bodies are linked by three different kinds of the link sections including the vertex-vertex bent link section, the central part-central part bent link section, and either the central part-vertex bent link section or the vertex-central part bent link section.

3. The stent according to claim 1, wherein all the axially adjacent annular bodies are linked by one of the vertex-vertex bent link sections, one of the central part-central part bent link sections, one of the central part-vertex bent link sections, and one of the vertex-central part bent link sections.

4. The stent according to claim 1, wherein the vertex-vertex bent link section linking first and second axially adjacent ones of the annular bodies is circumferentially offset from the vertex-vertex bent link section linking the second annular body to an axially adjacent third one of the annular bodies.

5. The stent according to claim 1, wherein the central part-central part bent link section linking first and second axially adjacent ones of the annular bodies is circumferentially offset from the central part-central part bent link section linking the second annular body to an axially adjacent third one of the annular bodies.

6. The stent according to claim 1, wherein the stent has a first linkage form in which the axially adjacent annular bodies are linked by at least the vertex-vertex bent link section and the central part-central part bent link section and a second linkage form in which the axially adjacent annular bodies are linked by at least the central part-vertex bent link section and the vertex-central part bent link section, the first linkage form and the second linkage form alternately repeating in the axial direction.

7. The stent according to claim 1, wherein the vertex-vertex bent link section has two one-end-side bent parts and two other-end-side bent parts.

8. The stent according to claim 1, wherein the central part-central part bent link section has only one one-end-side bent part and only one other-end-side bent part.

9. The stent according to claim 1, wherein the central part-vertex bent link section and the vertex-central part bent link section each have only one one-end-side bent part and only one other-end-side bent part.

10. The stent according to claim 1, wherein the one-end-side-bent part of the link section axially overlaps with the other-end-side bend sections of the one-end-side annular body of the axially adjacent annular bodies, and the other-end-side-bent part of the link section axially overlaps with the one-end-side bend sections of the other-end-side annular body of the axially adjacent annular bodies.

11. The stent according to claim 1, wherein the stent has the link sections so arranged that the same kind of the link sections are not continuously arrayed on a straight line in the axial direction of the stent.

12. The stent according to claim 1, wherein the stent is formed in a substantially cylindrical shape, is compressed toward its center axis when inserted into a living body, and is restored to its pre-compression shape through outward expansion when indwelled in the living body.

13. A stent delivery system comprising:
a stent-containing tubular member;
a stent according to claim 1 contained in a distal portion of the stent-containing tubular member; and
a releasing mechanism for releasing the stent via a distal end of the stent-containing tubular member.

14. A stent to be brought into contact with tissue in a living body through deformation at the time of indwelling the stent in the living body, the stent comprising:
at least four axially arranged and axially adjacent annular bodies, each of the at least four axially adjacent annular bodies being a wavy-shaped continuous linear member possessing: one-end-side bent sections, which are each a section of the linear member bent at a vertex on one axial end of the wavy-shaped linear member; and other-end-side bent sections which are each a section of the linear member bent at a vertex on an opposite axial end of the wavy-shaped linear member;

the at least four axially adjacent annular bodies being connected to one another by link sections;

the stent including as said link sections at least three different kinds of link sections selected from four different kinds of link sections, the four kinds of link sections including: a vertex-vertex bent link section which connects the vertex of one of the other-end-side bent sections of the one-end-side annular body of the axially adjacent annular bodies with the vertex of one of the one-end-side bent sections of the other-end-side annular bodies of the axially adjacent annular body and which has at least one one-end-side bent part and at least one other-end-side bent part; a central part-central part bent link section which connects a central part of a linear portion interconnecting the one-end-side bent section and the other-end-side bent section of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part; a central part-vertex bent link section which connects the central part of the linear portion interconnecting the one-end-side bent section and the other-end-side bent section of the one-end-side annular body of the axially adjacent annular bodies with the vertex of one of the one-end-side bent sections of the other-end-side annular body of the axially adjacent annular bodies and which has at least one one-end-side bent part and at least one other-end-side bent part; and a vertex-central part bent link section which connects the vertex of the other-end-side bent section of the one-end-side annular body of the axially adjacent annular bodies with a central part of a linear portion interconnecting the one-end-side bent section and the other-end-side bent section of the other-end-side annular body of the axially adjacent annular bodies and which has at least one one-end-side bent part and at least one other-end-side bent part;

the at least three kinds of the link sections including at least the vertex-vertex bent link section and the central part-central part bent link section, and the axially adjacent annular bodies being linked by at least two different kinds of the four link sections.

15. The stent according to claim 14, wherein:

the four axially adjacent annular bodies include a first annular body, a second annular body, a third annular body and a fourth annular body;

the first and second annular bodies are axially adjacent one another, the second and third annular bodies are axially adjacent one another, the third and fourth annular bodies are axially adjacent one another;

the first and the second axially adjacent annular bodies are connected to each other by one of the vertex-vertex bent link sections, one of the central part-central part bent link sections, one of the central part-vertex bent link sections and one of the vertex-central part bent link sections;

the second and the third axially adjacent annular bodies are connected to each other by one of the vertex-vertex bent link sections, one of the central part-central part bent link sections, one of the central part-vertex bent link sections and one of the vertex-central part bent link sections; and the third and the fourth axially adjacent annular bodies are connected to each other by one of the vertex-vertex bent link sections, one of the central part-central part bent link sections, one of the central part-vertex bent link sections and one of the vertex-central part bent link sections.

16. The stent according to claim 14, wherein:

the four axially adjacent annular bodies include a first annular body, a second annular body, a third annular body and a fourth annular body;

the first and second annular bodies are axially adjacent one another, the second and third annular bodies are axially adjacent one another, and the third and fourth annular bodies are axially adjacent one another;

the first and the second axially adjacent annular bodies are connected to each other by one of the vertex-vertex bent link sections, one of the central part-central part bent link sections and one of the central part-vertex bent link sections, and are not connected by one of the vertex-central part bent link sections;

the second and the third axially adjacent annular bodies are connected to each other by one of the vertex-vertex bent link sections, one of the central part-central part bent link sections and one of the central part-vertex bent link sections, and are not connected by one of the vertex-central part bent link sections; and the third and the fourth axially adjacent annular bodies are connected to each other by one of the vertex-vertex bent link sections, one of the central part-central part bent link sections and one of the central part-vertex bent link sections, and are not connected by one of the vertex-central part bent link sections.

17. The stent according to claim 14, wherein:

the four axially adjacent annular bodies include a first annular body, a second annular body, a third annular body and a fourth annular body;

the first and second annular bodies are axially adjacent one another, the second and third annular bodies are axially adjacent one another, the third and fourth annular bodies are axially adjacent one another;

the first and the second axially adjacent annular bodies are connected to each other by one of the vertex-vertex bent link sections, one of the central part-central part bent link sections and one of the vertex-central part bent link sections, and are not connected by one of the central part-vertex bent link sections;

the second and the third axially adjacent annular bodies are connected to each other by one of the vertex-vertex bent link sections, one of the central part-central part bent link sections and one of the vertex-central part bent link sections, and are not connected by one of the central part-vertex bent link sections; and the third and the fourth axially adjacent annular bodies are connected to each other by one of the vertex-vertex bent link sections, one of the central part-central part bent link sections and one of the vertex-central part bent link sections, and are not connected by one of the central part-vertex bent link sections.

18. The stent according to claim 14, wherein:

the four axially adjacent annular bodies include a first annular body, a second annular body, a third annular body and a fourth annular body;

the first and second annular bodies are axially adjacent one another, the second and third annular bodies are axially adjacent one another, the third and fourth annular bodies are axially adjacent one another;

the first and the second axially adjacent annular bodies are connected to each other by one of the vertex-vertex bent link sections and one of the vertex-central part bent link sections, and are not connected together by any of the central part-central part bent link sections and the central part-vertex bent link sections;

the second and the third axially adjacent annular bodies are connected to each other by one of the central part-central part bent link sections and one of the central part-vertex bent link sections, and are not connected together by any of the vertex-vertex bent link sections and the vertex-central part bent link sections;

the third and the fourth axially adjacent annular bodies are connected to each other by one of the vertex-vertex bent link sections and one of the vertex-central part bent link sections, and are not connected together by any of the central part-central part bent link sections and the central part-vertex bent link sections.

19. The stent according to claim 14, wherein:

the four axially adjacent annular bodies include a first annular body, a second annular body, a third annular body and a fourth annular body;

the first and second annular bodies are axially adjacent one another, the second and third annular bodies are axially adjacent one another, the third and fourth annular bodies are axially adjacent one another;

the first and the second axially adjacent annular bodies are connected to each other by one of the vertex-vertex bent link sections and one of the central part-central part bent link sections, and are not connected together by any of the central part-vertex bent link sections and the vertex-central part bent link sections;

the second and the third axially adjacent annular bodies are connected to each other by one of the central part-vertex bent link sections and one of the vertex-central part bent link section, and are not connected together by any of the vertex-vertex bent link sections and the central part-central part bent link sections;

the third and the fourth axially adjacent annular bodies are connected to each other by one of the vertex-vertex bent link sections and one of the central part-central part bent link sections, and are not connected together by any of the central part-vertex bent link sections and the vertex-central part bent link sections.

20. The stent according to claim 14, wherein axially successive ones of the vertex-vertex bent link sections are circumferentially offset from one another, and axially successive ones of the central part-central part bent link sections are circumferentially offset from one another.

* * * * *